United States Patent [19]
Kanteti et al.

[11] Patent Number: 6,010,853
[45] Date of Patent: Jan. 4, 2000

[54] SIVA GENES, NOVEL GENES INVOLVED IN CD27-MEDIATED APOPTOSIS

[75] Inventors: Prasad V. S. Kanteti, Boston, Mass.; Zhaohui Ao, Devon, Pa.; Stuart F. Schlossman, Newton Centre, Mass.

[73] Assignee: Dana-Farber Cancer Institute, Boston, Mass.

[21] Appl. No.: 08/865,297

[22] Filed: May 29, 1997

[51] Int. Cl.[7] .............................. C12Q 1/68; C07H 21/04; C12P 19/34; C12N 15/85

[52] U.S. Cl. ............................ 435/6; 435/91.4; 435/91.5; 435/69.1; 435/320.1; 435/325; 536/23.1; 536/23.4; 536/23.5

[58] Field of Search ................................... 536/23.1, 23.4, 536/23.5; 435/6, 69.1, 91.4, 91.5, 320.1, 325

[56] References Cited

U.S. PATENT DOCUMENTS

5,597,694  1/1997  Munroe et al. .............................. 435/6

FOREIGN PATENT DOCUMENTS

078771  3/1995  Japan .

OTHER PUBLICATIONS

Adams et al. (1993). GenBank, EST Data base. Accession No.: 659423. Publically available Aug. 19, 1993. (Also has ESTO1442 No.).

GenBank® Accession No. D90162 for, "Human DNA from chromosome 8 containing translocation breakpoint" Sep., 1990.

GenBank® Accession No. L42101 for, "Homo sapiens (subclone 10_g10 from P1 H23) DNA sequence" May, 1995.

GenBank® Accession No. L81793 for, "Homo sapiens (subclone 2_d6 from P1 H28) DNA sequence, complete sequence" Apr., 1997.

GenBank® Accession No. U51280 for, "Human chromosome 11 cosmid cSRL–183c2 containing Cys–tRNA synthetase (CARS) gene" Apr., 1996.

GenBank® Accession No. U52111 for "Human Xq28 genomic DNA in the region of the ALD locus containing the genes for creatine transporter (SLC6A8), CDM, adrenoleukodystrophy (ALD), Na+–isocitrate dehydrogenase gamma subunit (IDH), and translocon–associated protein delta (TRAP) genes, complete cds, plexin related protein (PLEXR) and serine kinase (SK) genes, partial cds, Xq281u1 gene and cytochrome C (CCp) pseudogene" Oct., 1996.

GenBank® Accession No. U52112 for, "Human Xq28 genomic DNA in the region of the L1CAM locus containing the genes for neural cell adhesion molecule L1 (L1CAM), arginine–vasopressin receptor (AVPR2), C1 p115 (C1), ARD1 N–acetyltransferase related protein (TE2), renin–binding protein (RbP), host cell factor 1 (HCF1), and interleukin–1 receptor–associated kinase (IRAK) genes, complete cds, and Xq281u2 gene" Oct., 1996.

GenBank® Accession No. U72789 for, "Human cosmid U197H5, complete sequence" Oct., 1996.

GenBank® Accession No. U80459 for, "Human Xq13 5' end of PAC 92E23 containing the X inactivation transcript (XIST) gene, complete sequence" Apr., 1997.

GenBank® Accession No. U81831 for, "Human cosmid LL12NC01–67C6, ETV6 gene, intron 1A, partial sequence" Jan., 1997.

GenBank® Accession No. U82213 for, "Human chromosome 10 clone LA10NC01_6_E_6, complete sequence" Jan., 1997.

Gen Bank® Accession No. U91323, "Human chromosome 16p13 BAC clone CIT987SK–972D3 complete sequence" Mar., 1997.

GenBank® Accession No. U91324 for, "Human chromosome 2 BAC clone CIT987SK–100B4 complete sequence" Mar., 1997.

GenBAnk® Accession No. U91325 for, "Human chromosome 16p13.11 BAC clone CIT987SK–731F11 complete sequence" Mar., 1997.

GenBank® Accession No. U95739 for, "Human chromosome 16p11.2–p12 BAC clone CIT987SK–224D6 complete sequence" Apr., 1997.

GenBank® Accession No. U95740 for, "Human chromosome 16p13.1 BAC clone CIT987SK–362G6 complete sequence" Apr., 1997.

GenBank® Accession No. U95742 for, "Human chromosome 16p13.1 BAC clone CIT987SK–551G9 complete sequence" Apr., 1997.

GenBank® Accession No. U96629 for, "Human chromosome 8 BAC clone CIT987SK–2A8 complete sequence" Apr., 1997.

GenBank® Accession No. Y08683 for, "H. sapiens mRNA for carnitine palmitoyltransferase I type II" Mar., 1997.

GenBank® Accession No. Y10196 for, "H sapiens PEX gene" Jul., 1997.

GenBank® Accession No. Z68129 for, "H. sapiens IDH gamma gene and TRAP delta gene" Jun., 1997.

GenBank® Accession No. Z68276 for, "Human DNA sequence from cosmid L190B4, Huntington's Disease Region, chromosome 4p16.3" Apr., 1996.

(List continued on next page.)

*Primary Examiner*—Nancy A Johnson
*Assistant Examiner*—Geetha P. Bansal
*Attorney, Agent, or Firm*—Lahive & cockfield, LLP; Amy E. Mandragouras, Esq.; Megan E. Williams, Ph.D.

[57] ABSTRACT

The invention provides isolated nucleic acids molecules, designated Siva nucleic acid molecules, which encode proteins involved in immune cell apoptosis. The invention also provides antisense nucleic acid molecules, recombinant expression vectors containing Siva nucleic acid molecules, host cells into which the expression vectors have been introduced, and nonhuman transgenic animals in which a Siva gene has been introduced or disrupted. The invention still further provides isolated Siva proteins, fusion proteins, antigenic peptides and anti-Siva antibodies. Diagnostic, screening, and therapeutic methods utilizing compositions of the invention are also provided.

16 Claims, 3 Drawing Sheets

OTHER PUBLICATIONS

GenBank® Accession No. Z68756 for, "Human DNA sequence from cosmid L191F1, Huntington's Disease Region, chromosome 4p16 3 contains Huntington Disease (HD) gene, CpG island ESTs and U7 small nuclear RNA" Mar., 1996.

GenBank® Accession No. Z70280 for, "Human DNA sequence from cosmid V210E9, between markers DXS366 and DXS87 on chromosome X" Mar., 1996.

GenBank® Accession No. Z73420 for, "Human DNA sequence from cosmid E146D10, on chromosome 22q11.2–qter, Contains rhodanese, rohu gene and ESTs" Jun., 1997.

GenBank® Accession No. Z73496 for, "Human DNA sequence from cosmid cU120E2, on chromosome X contains Lowe oculocerebrorenal syndrome (OCRL) ESTs and STS" Nov., 1996.

GenBank® Accession No. Z73967 for, "Human DNA sequence from cosmid 315B17, between markers DXS366 and DXS87 on chromosome X contains ESTs" Jun., 1996.

GenBGank® Accession No. Z73988 for, "Human DNA sequence from cosmid N120B6 on chromosome 22q12–qter" Jun., 1997.

GenBank® Accession No. Z74739 for, "Human DNA sequence from PAC 214K23, BRCA2 gene region chromosome 13q12–13 contains BRCA2 exons 1–24, Interferon Induced 56Kd pseudogene and ESTs" Apr., 1997.

GenBank® Accession No. Z75744 for, "Human DNA sequence from cosmid N117B5 on chromosome 22q12–qter contains EST" Jul., 1996.

GenBank® Accession No. Z79996 for, "Human DNA sequence from cosmid B33F2 on chromosome 22q11.2–qter contains ESTs" Jun., 1997.

GenBank® Accession No. Z81315 for, "Human DNA sequence from fosmid F62D4 on chromosome 22q12–qter" Oct., 1996.

GenBank® Accession No. Z81330 for, "Human DNA sequence from cosmid H2A1KLT on chromosome 9q34 contains ORFX gene, STS" Nov., 1996.

GenBank® Accession No. Z82205 for, "Human DNA sequence from PAC 363L9 on chromosome X, contains STS and polymorphic CA repeat" May, 1997.

GenBank® Accession No. Z82251 for, "Human DNA sequence from clone N87F1" Nov., 1996.

GenBank® Accession No. Z82975 for, "Human DNA sequence from PAC 36J3, between markers DXS1192 and DXS102 on chromosome X" Nov., 1996.

GenBank® Accession No. Z83820 for, "Human DNA sequence from PAC 215K18 on chromosome X contains ESTs and STS" Mar., 1997.

GenBank® Accession No. Z83821 for, "Human DNA sequence from PAC 296K21 on chromosome X contains cytokeratin exon, delta–aminolevulinate synthase (erythroid), 5–aminolevulinic acid synthase. (EC 2.3.1.37), 6–phosphofructo–2–kinase/fructose–2,6–bisphosphatase (EC 2.7.1.105, EC 3.1.3.46), ESTs and STS" Mar., 1997.

GenBank® Accession No. Z84474 for, "Human DNA sequence from PAC 111M5 on chromosome 6 Contains BBC1, RFP finger protein, EST, tRNAs, and polymorphic repeat" Mar., 1997.

GenBank® Accession No. Z86000 for, "Human DNA sequence from PAC 151B14 on chromosome 22q12–qter contains somatostatin receptor subtype 3 (SSTR3), tRNA, ESTs, CpG island and STS" Feb., 1997.

GenBank® Accession No. Z94057 for, "Human DNA sequence from PAC 518E13 on chromosome 1, Contains tenascin–R (restrictin) ESTs and STS" Jun., 1997.

GenBank® Accession No. AA506343 for, "ni15a11.s1 NCI_CGAP_Co4 Homo sapiens cDNA clone 968060 similar to gb:D38081 Thromboxane A2 Receptor (Human); contains element PTR5 repetitive element" Jul., 1997.

GenBank® Accession No. AC000003 for, "Genomic sequence from Human 17, complete sequence" Jun., 1997.

GenBank® Accession No. AC000045 for, "00064,complete sequence" Oct., 1996.

GenBank® Accession No. AC000063 for, "Human cosmid clone LUCA19 from 3p21.3, complete sequence" Nov., 1996.

GenBank® Accession No. AC000065 for, "Human BAC clone RG085C05 from 7q21–7q22, complete sequence" Nov., 1996.

GenBank® Accession No. AC000117 for, "Human BAD clone RG062A19 from 7q22, complete sequence" Jan., 1997.

GenBank® Accession No. AC000118 for, "Human BAC clone RG072E11 from 7q21–7q22, complete sequence" Jan., 1997.

GenBank® Accession No. AC000966 for, "Homo sapiens (subclone 1_a7 from P1 H28) DNA sequence, complete sequence" Apr., 1997.

GenBank® Accession No. AC001228 U90582 for, "244Kb Contig from Human Chromosome 11p15.5 spanning D11S1 through D11S25, complete sequence" Apr., 1997.

GenBank® Accession No. AC002040 for, "Homo sapiens Chromosome 16 BAC clone CIT987–SK142A6 complete genomic sequence, complete sequence" Jun., 1997.

GenBank® Accession No. AC002070 for, "Huamn BAC clone 7E17 from 12q, complete sequence" May, 1997.

GenBank® Accession No. AC002072 for, "Human PAC clone DJ218B13 from Xq23, complete sequence" May, 1997.

GenBank® Accession No. AC002074 for, "Human BAC clone GS056H18 from 7q31–q32, complete sequence" May, 1997.

GenBank® Accession No. AC002076 for, "Human BAC clone GS345D13 from 7q31–q32, complete sequence" May, 1997.

GenBank® Accession No. AC002314 for, "Human DNA from chromosome 19 cosmid R28052, genomic sequence, complete sequence" Jul., 1997.

GenBank® Accession No. AD000092 for, "Homo sapiens DNA from Chromosome 19p13.2 cosmids R31240, R30272 and R28549 containing the EKLF, GCDH, CRTC, and RAD23A genes, genomic sequence" Apr., 1997.

GenBank® Accession No. AD000823 for, "Homo sapiens DNA from chromosome 19–cosmid R31874, genomic sequence" Feb., 1997.

GenBank® Accession No. AD000827 for, "Homo sapiens DNA from chromosome 19–cosmid R31158" Feb., 1997.

GenBank® Accession No. AD000833 for "Homo sapiens DNA from chromosome 19–cosmid f19399 (~17 kb EcoRI restriction fragment)" Feb., 1997.

GenBank® Accession No. AF001548 for, "Homo sapiens chromosome 16 BAC clone CIT987SK–815A9 complete sequence" May., 1997.

GenBank® Accession No. AF001550 for, "Homo sapiens chromosome 16 BAC clone CIT987SK–334D11 complete sequence" May, 1997.

Abdulla, S. et al., "Divergent Intron Arrangement in the MB1/LMP7 Proteasome Gene Pair," *Immunogenetics*, vol. 44, 254–258 (1996).

Altschul, S.F. et al., "Basic Local Alignment Search Tool," *J. Mol. Biol.*, vol. 215, 403–410 (1990).

Andersson, B. et al., "Complete Sequence of a 38.4–kb Human Cosmid Insert Containing the Polymorphic Marker DXS455 from Xq28," *DNA Seq.*, vol. 5, No. 4, 219–223 (1995).

Andre, C. et al., "Sequence Analysis of Two Genomic Regions Containing the KIT and the FMS Receptor Tyrosine Kinase Genes," *Genomics*, vol. 39, 216–226 (1997).

Beck, S. et al., "Evolutionary Dynamics of Non–Coding Sequences Within the Class II Region of the Human MHC," *J. Mol. Biol.*, vol. 255, 1–13 (1996).

Bouffard, G.G. et al., "A Collection of 1814 Human Chromosome 7–Specific STSs," *Genome Res.*, vol. 7, 59–64 (1997).

Christmanson, L. et al., "The Human Islet Amyloid Polypeptide (IAPP) Gene Organization, Chromosomal Localization and Functional Identification of a Promote Region," *FEBS lett.*, vol. 267, No. 1, 160–166 (1990).

Claverie, J.M. and Makalowski, W., "Alu Alert," *Nature*, vol. 371 p. 752 (1994).

Francis, F. et al., "Genomic Organization of the Human PEX Gene Mutated in X–Linked Dominant Hypophosphatemic Rickets," *Genome Res.*, vol. 7, No. 6, 5735–85 (1997).

Gong, W. et al., "A Transcription Map of the DiGeorge and Velo–Cardio–Facial Syndrome Minimal Critical Region on 22q11," *Hum. Mol. Genet.*, vol. 5, No. 6, 789–800 (1996).

Gottlieb, S. et al., "The DiGeorge Syndrome Minimal Critical Region Contains a Goosecoid–like (GSCL) Homeobox Gene that is expressed Early in Human Development," *Am. J. Hum. Genet.*, vol. 60, 1194–1201 (1997).

Imbeaud, S. et al., "Insensitivity to Anti–Müllerian Hormone Due to a Mutation in the Human Anti–Müllerian Hormone Receptor," *Nat. Genet.*, vol. 11, 38238–8 (1995).

Jurka, J. and Milosavljevic, A., "Reconstruction and Analysis of Human Alu Genes," *J. Mol. Evol.*, vol. 32, 105–121 (1991).

Kato, N. et al., "Localization of the Rat Stimulatory G–Protein Alpha Subunit (GNPAS) Gene to Rat Chromosome 3 by Linkage Analysis," *Mamm. Genome*, vol. 7, No. 8, 628–629 (1996).

Kornreich, R. et al., "Nucleotide Sequence of the Human α–Galactosidase A Gene," *Nucleic Acids Res.*, vol. 17, no. 8, 3301–3302 (1989);.

Kuchinke, W. et al., "Identification of mRNAs Regulted by Interferon–γ in Cultured Rat Astrocytes by PCR Differential Display," *Neuroimmunomodulation*, vol. 2, 347–355 (1995).

Lamerdin, J.E. et al., "Sequence Analysis of the ERCC2 Gene Regions in Human, Mouse, and Hamster Reveals Three Linked Genes," *Genomics*, vol. 34, 399–409 (1996).

Lennard, A. et al., "Cloning and Chromosome Mapping of the Human Interleukin–1 Receptor Antagonist Gene," *Cytokine*, vol. 4, No. 2, 83–89 (1992).

Matassi, G. et al., "Characterization of the Recombination Hot Spot Involved in the Genomic Rearrangement Leading to the Hybrid D–CE–D Gene in the $D^{VI}$ Phenotype," *Am. J. Hum. Genet.*, vol. 60, 808–817 (1997).

Oeltjen, J.C. et al., "Sixty–nine Kilobases of Contiguous Human Genomic Sequence Containing the α–Galactosidase A and Bruton's Tyrosine Kinase Loci," *Mamm. Genome*, vol. 6, 334–338 (1995).

Pyerin, W., "Human Casein Kinase II: Structures, Genes, Expression and Requirement in Cell Growth Stimulation," *Advan. Enzyme Regul.*, vol. 34, 225–246 (1994).

Rao, E. et al., "Pseudoautosomal Deletions Encompassing a Novel Homeobox Gene Cause Growth Failure in Idiopathic Short Stature and Turner Syndrome," *nature Genet.*, vol. 16, 54–63 (1997).

Roark, J.H. et al., "Breakdown of B Cell Tolerance in a Mouse Model of Systemic Lupus Erythematosus," *J. Exp. Med.*, vol. 181, 1157–1167 (1995).

Sinnett, D. et al., "Alu RNA Transcripts in Human Embryonal Carcinoma Cells Model of Post–transcriptional Selection of Master Sequences," *J. Mol. Biol.*, vol. 226, 689–706 (1992).

Stenman, G. et al., "Regional Assignment of the Human 4–Hydroxyphenylpyruvate Dioxygenase Gene (HPD) to 12q24→qter by Fluorescence in Situ Hybridization," *Cytogenet. Cell Genet.*, vol.71, 374–376 (1995).

Tsukada, S. et al., "Deficient Expression of a B Cell Cytoplasmic Tyrosine Kinase in Human X–Linked Agammaglobulinemia," *Cell*, vol. 72, 279–290 (1993).

van Heyningen, V. and Little, P.F.R., "Report of the Fourth International Workshop on Human Chromosome 11 Mapping 1994" *Cytogenet. Cell Genet.*, vol. 69, 127–58 (1995).

Vetrie, D. et al., "The Gene Involved in X–Linked Agammaglobulinaemia is a Member of the src Family of Protein–Tyrosine Kinases," *Nature*, vol. 361, 226–233 (1993).

Virkkunen, P. et al., "Structural Comparison of Human and Rat Prostate–Specific Acid Phosphatase Genes and Their Promoters: Identificaton of Putative Androgen Response Elements," *Biochem. and Biophys. Res. Commun.*, vol. 202, no. 1, 49–57 (1994).

Vorechovsky, I. et al., "Isolation of Cosmid and cDNA Clones in the Region Surrounding the BTK Gene at Xq21.3–q22," *Genomics*, vol. 21, 517–524 (1994).

Wiginton, D.A. et al., "Complete Sequence and Structure of the Gene for Human Adenosine Deaminase," *Biochemistry*, vol. 25, 8234–8244 (1996).

Xiao, L. and Casero, R., "Differential Transcription of the Human Spermidine/Spermine $N^1$ –Acetyltransferase (SSAT) Gene in Human Lung Carcinoma Cells," *Biochem. J.*, vol. 313, 691–696 (1996).

Copy of GenBank® search using nucleotide sequence mouse siva gene.

Fitzgerald, L. A. et al., "Protein Sequence of Endothelial Glycoprotein IIIa Derived from a cDNA Clone," *J. Biol. Chem*, vol. 262, no. 9, 3936–3939 (1987).

Frachet, P. et al., "GPIIb and GPIIa Amino Acid Sequences Deduced from Human Megakaryocyte cDNAs," *Mol. Biol. Rep.*, vol. 14, 27–33 (1990).

Lanza, F. et al., "Characterization of the Human Platelet Glycoprotein IIIa Gene," *J. Biol. chem.*, vol. 265, no. 30, 18098–18103 (1990).

Prasad, K.V.S. et al., "CD27, a Member of the Tumor Necrosis Factor Receptor Family, Induces Apoptosis and Binds to Siva, a Proapoptotic Protein," *PNAS USA*, vol. 94, 6346–6351 (1997).

Zimrin, A.B. et al., "Structure of Platelet Glycoprotein IIIa A Common Subunit for Two Different Membrane Receptors," *J. Clin. Invest.*, vol. 81, 1470–1475 (1988).

Zimrin, A.B. et al., "The Genomic Organization of Platelet Glycoprotein IIIa," *J. Biol. Chem.*, vol. 265, No. 15, 8590–8595 (1990).

```
-132 AGCCAAGCGTGGTGGCATGTGCCTGTAATCCCAGCTACTCAGGAGGCTGAGGCATGAGAA

-72 TCTCTTGAACCCCAGAGGTGTAGGTTGCAGTGAGCAGAGATTGTGCCACTGCACTCCAGC

-12 CTGGGCGACAGCATGAGGCGGCCGGGGAGCTGCGTAGCTCCCGGCCCCGCGGCCATGCCC
                  M   R   R   P   G   S   C   V   A   P   G   P   A   A   M   P

49 AAGCGGAGCTGCCCCTTCGCGGACGTGGCCCCGCTACAGCTCAAGGTCCGCGTGAGCCAG
      K   R   S   C   P   F   A   D   V   A   P   L   Q   L   K   V   R   V   S   Q

109 AGGGAGTTGAGCCGCGGCGTGTGCGCCGAGCGCTACTCGCAGGAGGTCTTCGAGAAGACC
      R   E   L   S   R   G   V   C   A   E   R   Y   S   Q   E   V   F   E   K   T

169 AAGCGACTCCTGTTCCTCGGGGCCCAGGCCTACCTGGACCACGTGTGGGATGAAGGCTGT
      K   R   L   L   F   L   G   A   Q   A   Y   L   D   H   V   W   D   E   G   C

229 GCCGTCGTTCACCTGCCAGAGTCCCCAAAGCCTGGCCCTACAGGGGCCCCGAGGGCTGCA
      A   V   V   H   L   P   E   S   P   K   P   G   P   T   G   A   P   R   A   A

289 CGTGGGCAGATGCTGATTGGACCAGACGGCCGCCTGATCAGGAGCCTTGGGCAGGCCTCC
      R   G   Q   M   L   I   G   P   D   G   R   L   I   R   S   L   G   Q   A   S

349 GAAGCTGACCCATCTGGGGTAGCGTCCATTGCCTGTTCCTCATGCGTGCGAGCCGTGGAT
      E   A   D   P   S   G   V   A   S   I   A   C   S   S   C   V   R   A   V   D

409 GGGAAGGCGGTCTGCGGTCAGTGTGAGCGAGCCCTGTGCGGGCAGTGTGTGCGCACCTGC
      G   K   A   V   C   G   Q   C   E   R   A   L   C   G   Q   C   V   R   T   C

469 TGGGGCTGCGGCTCCGTGGCCTGTACCCTGTGTGGCCTCGTGGACTGCAGTGACATGTAC
      W   G   C   G   S   V   A   C   T   L   C   G   L   V   D   C   S   D   M   Y

529 GAGAAAGTGCTGTGCACCAGCTGTGCCATGTTCGAGACCTGAGGCTGGCTCAAGCCGGCT
      E   K   V   L   C   T   S   C   A   M   F   E   T

589 GCCTTCACCGGGAGCCACGCCGTGCATGGCAGCCTTCCCTGGACGAGCGCTCGGTGTTCA

649 GTGGGGTCGACGGGAGGGGTGCCTTTTACATGTTCTATTTTGTATCCTAATGACAGAATG

709 AATAAACCTCTTTATATTTGCAAAAAAAAAAAAAAAAAACTCGAG
```

FIGURE 1

```
1/1
TTT GGC TCC GAG GCC AAG AAT TCG GCA CGA GGG CTC GGC GCG CGG CGC GCT GCG CGC TGC
 F   G   S   E   A   K   N   S   A   R   G   L   G   A   R   R   A   A   R   C
61/21                                                   31/11
TGA AGG CTG TGT CTG GTA CCC GCT ACC ATG CCC AAG CGG AGC TGC CCG TTC GCA GAC GCA
 *   R   L   C   L   V   P   A   T   M   P   K   R   S   C   P   F   A   D   A
121/41                                  91/31
GCC CCG CTC CAA CTC AAA GTC CAC GTG GGC CTG AAA GAG CTG AGC CAC GGT GTG TTC GCC
 A   P   L   Q   L   K   V   H   V   G   L   K   E   L   S   H   G   V   F   A
181/61                                 151/51
GAG CGC TAC TCA CGC GAG GTC TTC GAA AGA ACC AAG CAG CTC CTT TTC CAA GGG GCT CGG
 E   R   Y   S   R   E   V   F   E   R   T   K   Q   L   L   F   Q   G   A   R
241/81                                 211/71
GCC TAT AGA GAT CAC ATA TCG AGC GAA GAT TGT TCC GTG AAC CAC CTG CAG GAG TCA CTG
 A   Y   R   D   H   I   S   S   E   D   C   S   V   N   H   L   Q   E   S   L
301/101                                271/91
AAG TCT GGT GTG GTA GGA GCC CCT CAA CCT GCG AGG GGA CAG ATG TTG ATT GGA CCT GAT
 K   S   G   V   V   G   A   P   Q   P   A   R   G   Q   M   L   I   G   P   D
361/121                                331/111
GGC CGA CTG ACA CGG TGC CAA GCT CAG GCC TCA GAA GGT GGC CTT CCC AGG ACA GCG CCC
 G   R   L   T   R   C   Q   A   Q   A   S   E   G   G   L   P   R   T   A   P
421/141                                391/131
ATC GCT TGT TCA TCG TGC ATG AGA TCT GTG GAT GGG AAG GCG GTC TGC AGC CAG TGC GAG
 I   A   C   S   S   C   M   R   S   V   D   G   K   A   V   C   S   Q   C   E
481/161                                451/151
CGG GCC CTG TGT CAG TGC GTA TAC ACC AGC TGG GGC TGC GGT GCT TTG GCC TGT TGT GTG
 R   A   L   C   Q   C   V   Y   T   S   W   G   C   G   A   L   A   C   C   V
541/181                                511/171
CTG TGT GGC CTT GCA GAC TAT GCC GAC GAT GGT GAG AAG ACA CTG TGC ACC AGC TGT GCT
 L   C   G   L   A   D   Y   A   D   D   G   E   K   T   L   C   T   S   C   A
                                       571/191
```

FIGURE 2A

```
601/201
ATG TTT GAA GCC TGA GGT GGC CAC AGA CAG ATG TTC ACA CTA AAG AGA GAG AAG
 M   F   E   A   *   G   G   H   R   Q   M   F   T   L   K   R   E   K
                                        631/211
661/221
GAG GCT TTT TAT ATG TTA TGT TTT ATA CCC AGT AAC AAG TGA ATA AAC CTC TTT ATA TTT
 V   A   F   Y   M   L   C   F   I   P   S   N   K   *   I   N   L   F   I   F
                                        691/231
721/241
GCA AAA AAA AAA AAA AAA AAA AAT TTC CGC GGC CGC AAG CTT AT
 A   K   K   K   K   K   K   N   F   R   G   R   K   L
```

FIGURE 2B

SIVA GENES, NOVEL GENES INVOLVED IN CD27-MEDIATED APOPTOSIS

BACKGROUND OF THE INVENTION

CD27 is a member of the tumor necrosis factor receptor (TNFR) super family which also includes TNFR type I and II (CD120a and b), nerve growth factor receptor (NGFR), CD30 (associated with Hodgkin's lymphoma), Fas/Apo-1 (CD95), CD40, 4-1 BB and OX40. These proteins are known to play a very important role in cell growth and differentiation as well as apoptosis or programmed cell death (Smith, C. A. et al. (1994) *Cell* 76:959–962). Homology among these family members is restricted to the extracellular region and is characterized by the presence of a cysteine knot motif which occurs three times in CD27 (McDonald, N. Q. and Hendrickson, W. A. (1993) *Cell* 73:421–424).

CD27 is a glycosylated, type I transmembrane protein of about 55 kd and exists as homodimers with a disulfide bridge linking the two monomers. The disulfide bridge is in the extracellular domain close to the membrane (Camerini, D. et al. (1991) *J. Immuuol.* 147:3165–3169; Gravestein, L. A. et al. (1993) *Eur. J. Immunol.* 23:943–950). The ligand for CD27, CD70, belongs to the TNF family of ligands. CD70 is a type II transmembrane protein with an apparent molecular weight of 50 kd (Goodwin R. G. et al. (1993) *Cell* 73:447–456; Bowman, M. R. et al. (1994) *J. Immunol.* 152:1756–1761). Based on homology to TNFα and TNFβ, especially in the β strands C, D, H and I, CD70 is predicted to have a trimeric structure made up of three identical subunits which possibly interact with three CD27 homodimers (Peitsch, M. C. and Tschopp, J. (1995) *Mol. Immunol.* 32:761–772). TNFα, which is also a type II transmembrane protein, is released from the cell by proteolytic cleavage, whereas TNFβ and NGF are secreted. So far there are no reports as to the existence of a naturally-occurring soluble form of CD70.

Expression of both CD27 and its ligand CD70 is restricted to discrete populations of both T and B cells. Although CD27 is expressed on the surface of resting T cells, CD70 appears only on activated T and B cells (Sugita, K. et al. (1992) *J. Immunol.* 149:3208–3216; Hintzen, R. Q. et al. (1993) *J. Immunol.* 151:2426–2435; Agematsu, K. et al. (1994) *J. Immunol.* 153:1421–1429; Hintzen, R. Q. et al. (1995) *J. Immunol.* 154:2612–2623). Within the T cell subsets, CD27 is stably expressed on the CD45RA+ population of T cells even after activation, whereas on CD45RO+ cells, it is weakly expressed and lost after activation (Sugita, K. et al. (1992) *J. Immunol.* 149:3208–3216; Hintzen, R. Q. et al. (1993) *J. Immunol.* 151:2426–2435). On CD45RA+ cells, activation by various means results in the up-regulation of CD27 expression (Hintzen, R. Q. et al. (1993) *J. Imminol.* 151:2426–2435; Maurer, D. et al. (1990) *Eur. J. Immunol.* 20:2679–2684). Although CD70 is not detectable on either CD45RA+ or CD45RO+ resting T cells, activation through the TcR/CD3 complex results in the expression of CD70 predominantly on CD45RO+ T cells. The reciprocal expression of CD27 and CD70 on subsets of helper cells suggested an important role for the molecules in T-T interactions, T cell activation, and regulation of immunoglobulin synthesis. Significant amounts of CD27 can also be detected on a subpopulation of B cells present in peripheral blood and tonsils (Maurer, R. Q. et al. (1995) *J. Immunol.* 154:2612–2623), and the expression can be enhanced after activation with PMA/ionomycin. CD27 is also expressed on the CD3-bright thymocytes and can be induced in low CD3, CD4+, CD8+ (double positive) cells following activation with ConA and PMA/ionomycin (Martorell, J. et al. (1990) *J. Immunol.* 145:1356–1363). In contrast, in murine systems CD27 is constitutively expressed on all thymocytes (Gravestein, L. A. et al. (1994) *Int. J. Immunol.* 7:551–557). A soluble form of CD27 (the extracellular region clipped by a protease) appears in the culture supernatant and can also be detected in the serum of normal individuals (Hintzen, R. Q. et al. (1991) *J. Neuroimmunol.* 35:211–218). CD27 is also highly expressed in most of the B cell non-Hodgkin's lymphomas and B cell chronic lymphocytic leukemias (Ranheim, E. A. et al. (1995) *Blood* 85:3556–3565; Van Oers, M. H. et al. (1993) *Blood* 82:3430–3436). The B cell lines, Ramos and Raji, express significant levels of both CD27 and its ligand CD70.

Ligation of CD27 along with treatment of T cells with sub-optimal dose of PMA, PHA, anti-CD2 or anti-CD3 antibodies results in the proliferation of T cells, thus defining a costimulatory role for CD27. The CD27-mediated costimulatory effect can be specifically inhibited by the addition of anti-CD27 antibody, or recombinant sCD27 or anti-CD70 antibody (Sugita, K. et al. (1992) *J. Immunol.* 149:3208–3216; Hintzen, R. Q. et al. (1993) *J. Immunol.* 151:2426–2435; Hintzen, R. Q. et al. (1995) *J. Immunol.* 154:2612–2623, Kobata, T. et al. (1994) *J. Immunol.* 153:5422–5432). CD27/CD70 interaction can also result in the generation of cytolytic T cells (Goodwin, R. G. et al. (1993) *Cell* 73:447–456). Ligation of CD27 with CD70 on B cells significantly enhances IgG production, with a less pronounced effect on cell proliferation (Kobata, T. et al. (1995) *PNAS* 92:11249–11253). These studies clearly emphasize the importance of CD27/CD70 binding in both T-T, T-B and B-B cell interactions. Unlike CD28, CD27-mediated T cell proliferation does not support secretion of large amounts of IL2, clearly defining a different role for CD27/CD70 coupled co-stimulatory pathways. The CD45RA+ T cells which express CD27 are poor producers of IL2 and IL4 (Sugita, K. et al. (1992) *J. Immunol.* 151:2426–2435), as opposed to CD28 where coligation with TcR/CD3 complex results in elevated levels of IL2.

Thus, as CD27/CD70 binding is important in both T-T, T-B, and B-B cell interactions, it would be desirable to further elucidate the role of CD27 in T and B cell signaling.

SUMMARY OF THE INVENTION

This invention provides novel nucleic acid molecules which encode proteins, referred to herein as Siva proteins, which are capable of, for example, modulating apoptosis, e.g., apoptosis of immune cells. Nucleic acid molecules encoding the Siva proteins are referred to herein as Siva nucleic acid molecules. In a preferred embodiment, the Siva proteins interact with (e.g., bind to) CD27 or a portion thereof, e.g., the cytoplasmic tail of CD27, to modulate CD27-mediated immune cell apoptosis. As described herein, the Siva molecules (or modulators thereof) of the invention can be used to treat proliferative disorders, e.g., proliferative disorders of immune cells and autoimmune diseases, and to inhibit metastasis of tumor cells.

Accordingly, one aspect of the invention pertains to isolated nucleic acid molecules (e.g., cDNAs) comprising a nucleotide sequence encoding a Siva protein or portions thereof (e.g., biologically active or antigenic portions), as well as nucleic acid fragments suitable as primers or hybridization probes for the detection of Siva-encoding nucleic acid (e.g., mRNA). In particularly preferred embodiments, the isolated nucleic acid molecule comprises the nucleotide sequence of SEQ ID NO:1 or SEQ ID NO:3. In other particularly preferred embodiments, the isolated nucleic acid molecule of the invention comprises a nucleotide sequence which hybridizes to or is at least about 75.5, 76, 77, 78, 79%, more preferably at least about 80%, even more preferably at least about 85%, still more preferably at least about 90%, and most preferably at least about 95% or more homologous to the nucleotide sequence shown in SEQ ID NO:1 or a portion thereof. In still other particularly preferred embodiments, the isolated nucleic acid molecule of the invention comprises a nucleotide sequence which hybridizes to or is at least about 65%, preferably at least about 70%, more preferably at least about 75%, even more preferably at least about 80%, still more preferably at least about 85%, still more preferably at least about 90%, and most preferably at least about 95% or more homologous to the nucleotide sequence shown in SEQ ID NO:3 or a portion thereof. In other preferred embodiments, the isolated nucleic acid molecule encodes the amino acid sequence of SEQ ID NO:2 or SEQ ID NO:4 or a portion thereof. The preferred Siva proteins, e.g., Siva-1 and Siva-2, of the present invention also preferably possess at least one of the Siva biological activities described herein.

In another embodiment, the isolated nucleic acid molecule encodes a protein or portion thereof wherein the protein or portion thereof includes an amino acid sequence which is sufficiently homologous to an amino acid sequence of SEQ ID NO:2 or SEQ ID NO:4 such that the protein or portion thereof maintains a Siva biological activity. Preferably, the protein or portion thereof encoded by the nucleic acid molecule maintains the ability to modulate apoptosis, e.g., apoptosis of an immune cell. In one embodiment, the protein encoded by the nucleic acid molecule is at least about 71, 72, 73, 74, 75, 76, 77, 78, 79%, preferably at least about 80%, more preferably at least about 85%, even more preferably at least about 90%, and most preferably at least about 95% or more homologous to the amino acid sequence of SEQ ID NO:2 (e.g., the entire amino acid sequence of SEQ ID NO:2). In another preferred embodiment, the protein encoded by the nucleic acid molecule is at least about 65%, preferably at least about 70%, more preferably at least about 75%, even more preferably at least about 80%, still more preferably at least about 90%, and most preferably at least about 95% or more homologous to the amino acid sequence shown in SEQ ID NO:4 (e.g., the entire amino acid sequence of SEQ ID NO:4).

In yet another embodiment, the isolated nucleic acid molecule is derived from a human and encodes a portion of a protein which includes one or more of the following domains: a) a death domain homology region which is at least about 50% homologous to the amino acid sequence of SEQ ID NO:7 or SEQ ID NO:10; b) a zinc finger domain which is at least about 50% homologous to the amino acid sequence of SEQ ID NO:8 or SEQ ID NO:11; and c) a B-Box like ring finger domain which is at least about 50% homologous to the amino acid sequence of SEQ ID NO:9 or SEQ ID NO:12 and has one or more of the following biological activities: 1) it is capable of modulating apoptosis, e.g., apoptosis of an immune cell; 2) it can interact with (e.g., bind to) CD27 or a portion thereof, e.g., the cytoplasmic tail of CD27; and 3) it can modulate the activity of CD27.

In another embodiment, the isolated nucleic acid molecule is at least 15 nucleotides (e.g., at least 20, 30, 40, 50, 60, 70, 80, 90, 100, 200, 300, 400, 500, or more) in length and hybridizes under stringent conditions to a nucleic acid molecule comprising the nucleotide sequence of SEQ ID NO:1 or SEQ ID NO:3. Preferably, the isolated nucleic acid molecule corresponds to a naturally-occurring nucleic acid molecule. More preferably, the isolated nucleic acid encodes naturally-occurring human Siva-1 or human Siva-2 or a biologically active portion thereof. Moreover, given the disclosure herein of Siva-encoding cDNA sequences (e.g., SEQ ID NO:1 and SEQ ID NO:3), antisense nucleic acid molecules (i.e., molecules which are complementary to the coding strand of the Siva cDNA sequences) are also provided by the invention.

Another aspect of the invention pertains to vectors, e.g., recombinant expression vectors, containing the nucleic acid molecules of the invention and host cells into which such vectors have been introduced. In one embodiment, such a host cell is used to produce Siva protein by culturing the host cell in a suitable medium. If desired, the Siva protein can be then isolated from the medium or the host cell.

Yet another aspect of the invention pertains to transgenic nonhuman animals in which a Siva gene has been introduced or altered. In one embodiment, the genome of the nonhuman animal has been altered by introduction of a nucleic acid molecule of the invention encoding Siva as a transgene. In another embodiment, an endogenous Siva gene within the genome of the nonhuman animal has been altered, e.g., functionally disrupted, by homologous recombination.

Still another aspect of the invention pertains to an isolated Siva protein, e.g., Siva-1 and Siva-2. or a portion, e.g., a biologically active portion, thereof. In a preferred embodiment, the isolated Siva protein or portion thereof can modulate apoptosis, e.g., apoptosis of an immune cell. In another preferred embodiment, the isolated Siva protein or portion thereof is sufficiently homologous to an amino acid sequence of SEQ ID NO:2 or SEQ ID NO:4 such that the protein or portion thereof maintains the ability to modulate apoptosis, e.g., apoptosis of an immune cell.

In one embodiment, the portion of the Siva protein includes a domain or motif, preferably a domain or motif which has a Siva biological activity. The domain can be a death domain homology region, a zinc finger domain, or a B-Box like ring finger domain. If the biologically active portion is derived from Siva-1, the death domain homology region is preferably at least about 50% homologous to the amino acid sequence of SEQ ID NO:7, the zinc finger domain is preferably at least about 50% homologous to the amino acid sequence of SEQ ID NO:8; and the B-Box like ring finger domain is preferably at least about 50% homologous to the amino acid sequence of SEQ ID NO:9. If the biologically active portion is derived from Siva-2, the death domain homology region is preferably at least about 50% homologous to the amino acid sequence of SEQ ID NO:10, the zinc finger domain is preferably at least about 50% homologous to the amino acid sequence of SEQ ID NO:11; and the B-Box like ring finger domain is preferably at least about 50% homologous to the amino acid sequence of SEQ ID NO:12. Preferably, the biologically active portion of the Siva protein which includes one or more of these domains also has one of the following biological activities: 1) it is capable of modulating apoptosis, e.g., apoptosis of an immune cell; 2) it can interact with (e.g., bind to) CD27 or a portion thereof, e.g., the cytoplasmic tail of CD27; and 3) it can modulate the activity of CD27.

The invention also provides an isolated preparation of a Siva protein. In preferred embodiments, the Siva protein comprises the amino acid sequence of SEQ ID NO:2 or SEQ ID NO:4. In one preferred embodiment, the protein is at least about 71, 72, 73, 74, 75, 76, 77, 78, 79%, preferably at least about 80%, more preferably at least about 85%, even more preferably at least about 90%, and most preferably at least about 95% or more homologous to the amino acid sequence of SEQ ID NO:2 (e.g., the entire amino acid sequence of SEQ ID NO:2). In another preferred embodiment, the protein is at least about 65%, preferably at least about 70%, more preferably at least about 80%, even more preferably at least about 85%, still more preferably at least about 90%, and most preferably at least about 95% or more homologous to the amino acid sequence shown in SEQ ID NO:4 (e.g., the entire amino acid sequence of SEQ ID NO:4). Alternatively, the isolated Siva protein comprises an amino acid sequence which is encoded by a nucleotide sequence which hybridizes, e.g., hybridizes under stringent conditions, or is at least about 75.5, 76, 77, 78, 79%, more preferably at least about 80%, even more preferably at least about 85%, still more preferably at least about 90%, and most preferably at least about 95% or more homologous to the nucleotide sequence shown in SEQ ID NO:1. In another embodiment, the isolated Siva protein comprises an amino acid sequence which is encoded by a nucleotide sequence which hybridizes, e.g., hybridizes under stringent conditions, or is at least about 65%, preferably at least about 70%, more preferably at least about 75%, even more preferably at least about 80%, still more preferably at least about 85%, still more preferably at least about 90%, and most preferably at least about 95% or more homologous to the nucleotide sequence shown in SEQ ID NO:3. It is also preferred that the preferred forms of Siva possess one or more of the Siva biological activities described herein.

The Siva protein (or polypeptide) or a biologically active portion thereof can be operatively linked to a non-Siva polypeptide to form a fusion protein. In addition, the Siva protein or a biologically active portion thereof can be incorporated into a pharmaceutical composition comprising the protein and a pharmaceutically acceptable carrier.

The Siva protein of the invention, or portions or fragments thereof, can be used to prepare anti-Siva antibodies. Accordingly, the invention also provides an antigenic peptide of Siva which comprises at least 8 amino acid residues of the amino acid sequence shown in SEQ ID NO:2 or SEQ ID NO:4 and encompasses an epitope of Siva such that an antibody raised against the peptide forms a specific immune complex with Siva. Preferably, the antigenic peptide comprises at least 10 amino acid residues, more preferably at least 15 amino acid residues, even more preferably at least 20 amino acid residues, and most preferably at least 30 amino acid residues. The invention further provides an antibody that specifically binds Siva. In one embodiment, the antibody is monoclonal. In another embodiment, the antibody is coupled to a detectable substance. In yet another embodiment, the antibody is incorporated into a pharmaceutical composition comprising the antibody and a pharmaceutically acceptable carrier.

Another aspect of the invention pertains to methods for modulating a cell associated activity, e.g., proliferation, differentiation, survival. Such methods include contacting the cell with an agent which modulates Siva protein activity or Siva nucleic acid expression such that a cell associated activity is altered relative to a cell associated activity (e.g., the same cell associated activity) of the cell in the absence of the agent. In a preferred embodiment, the cell is an immune cell (e.g., a T cell or a B cell). The agent which modulates Siva activity can be an agent which stimulates Siva protein activity or Siva nucleic acid expression. Examples of agents which stimulate Siva protein activity or Siva nucleic acid expression include small molecules such as small organic or inorganic molecules, active Siva proteins, and nucleic acids encoding Siva that have been introduced into the cell. Examples of agents which inhibit Siva protein activity or nucleic acid expression include small molecules, antisense Siva nucleic acid molecules, and antibodies that specifically bind to Siva.

The present invention also pertains to methods for treating subjects having various disorders. For example, the invention pertains to methods for treating a subject having a disorder characterized by aberrant Siva protein activity or nucleic acid expression such as a proliferative disorder (cancer), e.g., a proliferative disorder of an immune cell, or an autoimmune disease, e.g., multiple sclerosis. These methods include administering to the subject a Siva modulator (e.g., a small molecule, an antibody, a nucleic acid encoding a Siva protein or portion, a Siva protein or portion thereof) such that treatment of the subject occurs.

The invention also pertains to methods for detecting genetic lesions in a Siva gene, thereby determining if a subject with the lesioned gene is at risk for (or is predisposed to have) a disorder characterized by aberrant or abnormal Siva nucleic acid expression or Siva protein activity, e.g., a proliferative disorder or an autoimmune disease. The methods include detecting, in a sample of cells from the subject, the presence or absence of a genetic lesion characterized by an alteration affecting the integrity of a gene encoding a Siva protein, or the misexpression of a Siva gene.

Another aspect of the invention pertains to methods for detecting the presence of Siva in a biological sample. In a preferred embodiment, the methods involve contacting a biological sample (e.g., an immune cell, e.g., a peripheral blood lymphocyte) with a compound or an agent capable of detecting Siva protein or Siva mRNA such that the presence of Siva is detected in the biological sample. The compound or agent can be, for example, a labeled or labelable nucleic acid probe capable of hybridizing to Siva mRNA or a labeled or labelable antibody capable of binding to Siva protein.

The invention further provides methods for diagnosis of a subject with, for example, a proliferative disorder or an autoimmune disease, based on detection of Siva protein or mRNA. In one embodiment, the method involves contacting a cell or tissue sample (e.g., a peripheral blood lymphocyte sample) from the subject with an agent capable of detecting Siva protein or mRNA, determining the amount of Siva protein or mRNA expressed in the cell or tissue sample, comparing the amount of Siva protein or mRNA expressed in the cell or tissue sample to a known standard or control sample and forming a diagnosis based on the amount of Siva protein or mRNA expressed in the cell or tissue sample as compared to the standard or control sample. Preferably, the cell sample is an immune cell sample. Kits for detecting Siva in a biological sample are also within the scope of the invention.

Still another aspect of the invention pertains to methods, e.g., screening assays, for identifying a compound for treating a disorder characterized by aberrant Siva nucleic acid expression or protein activity, e.g., a proliferative disorder or an autoimmune disease. These methods typically include assaying the ability of the compound or agent to modulate the expression of a Siva gene or the activity of a Siva protein. In a preferred embodiment, the method involves contacting a biological sample (e.g., a cell or tissue sample, e.g., an immune cell sample such as a peripheral blood lymphocyte sample) obtained from a subject having the disorder with the compound or agent, comparing the amount of Siva protein expressed and/or measuring the activity of the Siva protein in the presence or absence of the compound or agent. An alteration in the amount of Siva nucleic acid expression or Siva protein activity in the cell exposed to the compound or agent in comparison to the unexposed sample is indicative of a modulation of Siva nucleic acid expression and/or Siva protein activity.

The invention also pertains to methods for identifying a compound or agent which interacts with (e.g., binds to) a Siva protein. These methods can include the steps of contacting the Siva protein with the compound or agent under conditions which allow binding of the compound to the Siva protein to form a complex and detecting the formation of a complex of the Siva protein and the compound in which the ability of the compound to bind to the Siva protein is indicated by the presence of the compound in the complex.

The invention further pertains to methods for identifying a compound or agent which modulates, e.g., stimulates or inhibits, the interaction of a Siva protein with a target molecule, e.g., CD27 or a portion thereof, e.g., the cytoplasmic tail of CD27. In these methods, the Siva protein is contacted, in the presence of the compound or agent, with the target molecule under conditions which allow binding of the target molecule to the Siva protein to form a complex. An alteration, e.g., an increase or decrease, in complex formation between the Siva protein and the target molecule as compared to the amount of complex formed in the absence of the compound or agent is indicative of the ability of the compound or agent to modulate the interaction of the Siva protein with a target molecule.

BRIEF DESCRIPTION OF THE DRAWINGS

FIG. 1 depicts the nucleotide (SEQ ID NO:1) and deduced amino acid (SEQ ID NO:2) sequence of the human Siva-1 gene including 5' and 3' untranslated regions.

FIG. 2 depicts the nucleotide (SEQ ID NO:5) and deduced amino acid (SEQ ID NO:6) sequence of the mouse Siva gene without the 5' and 3' untranslated regions.

DETAILED DESCRIPTION OF THE INVENTION

The present invention is based on the discovery of novel molecules, referred to herein as Siva nucleic acid and protein molecules, which play a role in or function in programmed cell death or apoptosis. The Siva molecules, which are named after Siva, the Hindu god of destruction, were discovered based, at least in part, on experiments using the cytoplasmic tail of human CD27 as bait in a yeast two hybrid system to identify novel CD27-interacting proteins.

The human Siva-1 nucleotide sequence (identified as described in Example I) and the predicted amino acid sequence of the human Siva-1 protein are shown in FIG. 1 and in SEQ ID NOs:1 and 2, respectively. The nucleotide sequence of Siva-1 has been deposited with GenBank and assigned Accession Number U2938. The human Siva-1 gene, which is approximately 885 nucleotides in length (the coding region is approximately 567 nucleotides in length), encodes a full length protein which is approximately 189 amino acid residues in length.

The Siva-1 protein is rich in cysteines and contains several domains. These domains include a) a death domain homology region (DDHR) which appears at amino acid residues 62 to 136 of SEQ ID NO:2 and which is also shown in the present application as a separate sequence designated SEQ ID NO:7. As used herein, a DDHR refers to a region of a Siva protein which includes at least about 40, preferably at least about 50, more preferably at least about 60, still more preferably at least about 70, and most preferably at least about 80 amino acid residues or more and which is at least about 10% or more homologous to the death domain of FADD (Chinnaiyan, A. M. et al. (1995) Cell 81:505–512), RIP (Stanger, B. Z. et al. (1995) Cell 81:513–523), TRADD (Hsu, H. et al. (1995) Cell 81:495–504), or Fas (Cleveland, J. L. and Ihle, J. N. (1995) Cell 81:479–482). The DDHR typically is a region of a protein which is involved in apoptosis. The DDHR can also be involved in, for example, modulation of transcription. In one embodiment, the DDHR of Siva is involved in activation of transcription factors such as NFkB. Methods for measuring NFkB activation are known in the art. Hsu, H. et al. (1995) Cell 81:495–504. In preferred embodiments, a Siva protein of the invention includes a DDHR which is at least about 50%, more preferably at least about 60%, still more preferably at least about 70%, and most preferably at least about 80, 85, 90% or more homologous to the DDHR of Siva-1 as shown in SEQ ID NO:7.;

b) a zinc finger domain at amino acid residues 164–184 of SEQ ID NO:2 and which is also shown in the present application as a separate sequence designated SEQ ID NO:8. As used herein, a zinc finger domain refers to a region of a Siva protein which comprises at least about 20 amino acid residues and which includes at least about 4, more preferably at least about 5 or more cysteine residues. The zinc finger domain is typically involved in binding of the Siva protein to another protein or to a nucleic acid. For example, the zinc finger domain of Siva can be involved in modulating gene transcription in cells, e.g., immune cells. In preferred embodiments, a Siva protein of the invention includes a zinc finger domain which is at least about 50%, more preferably at least about 60%, still more preferably at least about 70%, and most preferably at least about 80, 85, 90% or more homologous to the zinc finger domain of Siva-1 as shown in SEQ ID NO:8; and c) and a B-box like ring finger domain at amino acid residues 128–159 of SEQ ID NO:2 and which is also shown in the present application as a separate sequence designated SEQ ID NO:9. This B-box like ring finger lacks histidine. As used herein, a B-box like ring finger domain refers to a region of a Siva protein which comprises at least about 20, more preferably at least about 30 or more amino acid residues and which includes at least about 5, preferably at least about 6, more preferably at least about 7, and most preferably at least about 8 or more cysteine residues. The B-Box like ring finger domain can be involved in, for example, modulation of transcription. In one embodiment, the B-Box like ring finger domain of Siva is involved in activation of transcription factors such as NFkB. In preferred embodiments, a Siva protein of the invention includes a B-Box like ring finger domain which is at least about 50%, more preferably at least about 60%, still more preferably at least about 70%, and most preferably at least about 80, 85, 90% or more homologous to the B-Box like ring finger domain of Siva-1 as shown in SEQ ID NO:9.

Since the cysteine rich carboxy terminus of the Siva-1 protein, which includes both the zinc finger domain and the B-box like ring finger domain, was present in the original yeast insert H2 used in the yeast two hybrid assays which led to the discovery of the Siva molecules, the cysteine rich carboxy terminus likely mediates binding to CD27, e.g., the CD27 cytoplasmic tail. Moreover, it is known that carboxy terminal zinc fingers are involved in mediating protein-protein interactions (Freemont, P. S. (1993) *Ann. N.Y. Acad. Sci.* 684:174–192). Thus, as used herein, the language "CD27-binding domain" refers to the combined zinc finger and B-box like ring finger domain of the Siva protein.

Using Northern analysis, the Siva-1 protein was found to be expressed in spleen, thymus, prostate, testis, ovary, small intestine, colon, and peripheral blood lymphocytes as well as several cell lines including HeLa cells (ATCC Accession No. CCL 2: human cervical carcinoma cell line), Raji cells (ATCC Accession No. CCL 86: human Burkitt lymphoma cell line), HL60 cells (ATCC Accession No. CCL 240: human promyclocyte cell line), K562 cells (ATCC Accession No. CCL 243: human erythroleukemia cell line), MOTL-4 cells (ATCC Accession No. CRL 1582: human acute lymphoblastic leukemia cell line), SW480 cells (ATCC Accession No. CCL 228: human colorectal adenocarcinoma cell line), A549 cells (ATCC Accession No. CCL 185: human lung carcinoma cell line), and G-361 cells (ATCC Accession No. CRL 1424: human malignant melanoma cell line).

During a screen of a human thymus cDNA library using a partial clone of Siva-1 to obtain the full length Siva-1 nucleic acid molecule, a second Siva nucleic acid molecule, which appears to be an alternate splice form of Siva-1, was identified. The alternate splice form of Siva-1 was named Siva-2. The Siva-2 nucleic acid molecule is the same as that of Siva-1 except that it includes a large in-frame deletion of nucleotides 157–351 of the nucleotide sequence shown in FIG. 1 (nucleotides 289–483 of SEQ ID NO:1). The human Siva-2 nucleotide sequence (identified as described in Example VI) and the predicted amino acid sequence of the human Siva-2 protein are shown in SEQ ID NOs:3 and 4, respectively. The human Siva-2 cDNA, which is approximately 690 nucleotides in length (the coding region is approximately 372 nucleotides in length), encodes a full length protein which is approximately 124 amino acid residues in length. The Siva-2 protein is rich in cysteines and contains several domains including a portion of the death domain homology region (DDHR) of Siva-1 at amino acid residues 54 to 118 of SEQ ID NO:4 and which is also shown in the present application as a separate sequence designated SEQ ID NO:10, a zinc finger domain at amino acid residues 99 to 119 of SEQ ID NO:4 and which is also shown in the present application as a separate sequence designated SEQ ID NO:11, and a B-box like ring finger domain at amino acid residues 63 to 94 of SEQ ID NO:4 and which is also shown in the present application as a separate sequence designated SEQ ID NO:12. The cysteine rich carboxy terminus of zinc finger domain and the B-box like ring finger domain together comprise a CD27-binding domain. As the Siva-2 protein lacks most of the DDHR of the Siva-1 protein, the Siva-2 protein may be a naturally-occurring dominant negative regulatory form of Siva-1 and thus may be able to inhibit the proapoptotic activity of Siva-1.

A mouse homologue of Siva-1 was identified by sequencing the mouse cDNA insert of ATCC Accession No. 738252 and comparing it to the Siva-1 nucleotide sequence. The nucleotide sequence of the mouse homologue (shown in SEQ ID NO:5) was found to be about 75% homologous to the nucleotide sequence of Siva-1. The amino acid sequence of the mouse homologue (shown in SEQ ID NO:6) was found to be about 70.3% homologous to the amino acid sequence of Siva-1.

The Siva proteins or biologically active portions thereof of the invention can have one or more of the following biological activities: 1) they can interact with (e.g., bind to) CD27, e.g., the cytoplasmic tail of CD27; 2) they can modulate the activity of CD27; and 3) they can modulate or regulate apoptosis, e.g., apoptosis of immune cells. Thus, in a preferred embodiment of the invention, the Siva molecules modulate CD27-mediated apoptosis of cells, e.g., immune cells. As used herein, the language "immune cell" refers to hematopoictic cells such as T lymphocytes, B lymphocytes, monocytes, macrophages, dendritic cells, and other antigen presenting cells, natural killer (NK) cells, and lymphokine activated killer (LAK) cells. Thus, as elevated levels of solible CD27 have been reported in cases of multiple sclerosis (Hinzten, R. Q. et al. (1991) *J. Neuroimmunol.* 35:211–218), and such elevated levels may inhibit the regulatory or other effects of CD70-expressing and B cells, the Siva molecules (or modulators thereof) of the invention, which can modulate the activity of CD27, can be used to treat multiple sclerosis and other autoimmune diseases. It is also known that B cell cancers such as Non-Hodgkin's lymphoma and B cell chronic lymphocytic leukemia (B-CLL) do not undergo apoptosis despite the high expression of both CD27 and CD70. This is due to the fact that these cells release soluble CD27 which builds up in the body fluids and disrupts CD27-mediated apoptosis. Thus, the Siva molecules (or modulators thereof) of the invention can also be used to treat immune cell proliferative disorders such as Non-Hodgkin's lymphoma and leukemias. Moreover, disruption of binding between CD27 and CD70 by soluble CD27 aids in metastasis by, for example, loosening the homotypic cell—cell contact occurring through CD27 and CD70 interaction. By promoting apoptosis of the tumorigenic cells, the Siva molecules (or modulators thereof) of the invention can be used to inhibit tumor metastasis.

Various aspects of the invention are described in further detail in the following subsections:

I. Isolated Nucleic Acid Molecules

One aspect of the invention pertains to isolated nucleic acid molecules that encode Siva or biologically active portions thereof, as well as nucleic acid fragments sufficient for use as primers or hybridization probes to identify Siva-encoding nucleic acid (e.g., Siva mRNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated Siva nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., an immune cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of SEQ ID NO:1 or SEQ ID NO:3, or a portion thereof, can be isolated using standard molecular biology techniques and the sequence information provided herein. For example, a human Siva cDNA can be isolated from a human thymus library using all or portion of SEQ ID NO:1 or SEQ ID NO:3 as a hybridization probe and standard hybridization techniques (e.g., as described in Sambrook, J., Fritsh, E. F., and Maniatis, T. *Molecular Cloning: A Laboratory Manual. 2nd, ed, Cold Spring Harbor Laboratory*, Cold Spring Harbor Laboratory Press, Cold Spring Harbor, N.Y., 1989). Moreover, a nucleic acid molecule encompassing all or a portion of SEQ ID NO:1 or SEQ ID NO:3 can be isolated by the polymerase chain reaction using oligonucleotide primers designed based upon the sequence of SEQ ID NO:1 or SEQ ID NO:3, respectively. For example, mRNA can be isolated from immune cells, e.g., peripheral blood lymphocytes (e.g., by the guanidinium-thiocyanate extraction procedure of Chirgwin et al. (1979) *Biochemistry* 18: 5294–5299) and cDNA can be prepared using reverse transcriptase (e.g., Moloney MLV reverse transcriptase, available from Gibco/BRL, Bethesda, M.d.; or AMV reverse transcriptase, available from Scikagaku America, Inc., St. Petersburg, Fla.). Synthetic oligonucleotide primers for PCR amplification can be designed based upon the nucleotide sequence shown in SEQ ID NO:1 or SEQ ID NO:3. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a Siva nucleotide sequence can be prepared by standard synthetic techniques, e.g., using an automated DNA synthesizer.

In a preferred embodiment, an isolated nucleic acid molecule of the invention comprises the nucleotide sequence shown in SEQ ID NO:1 or SEQ ID NO:3. The sequence of SEQ ID NO:1 corresponds to the human Siva-1 cDNA. This cDNA comprises sequences encoding the Siva-1 protein (i.e., "the coding region", from nucleotides 133 to 699), as well as 5' untranslated sequences (nucleotides 1 to 132) and 3' untranslated sequences (nucleotides 700 to 885). Alternatively, the nucleic acid molecule can comprise only the coding region of SEQ ID NO:1 (e.g., nucleotides 133 to 699). The sequence of SEQ ID NO:3 corresponds to the human Siva-2 cDNA. This cDNA comprises sequences encoding the Siva-2 protein (i.e., "the coding region", from nucleotides 133 to 504), as well as 5' untranslated sequences (nucleotides 1 to 132) and 3' untranslated sequences (nucleotides 505 to 690). Alternatively, the nucleic acid molecule can comprise only the coding region of SEQ ID NO:3 (e.g., nucleotides 133 to 504).

In another preferred embodiment, an isolated nucleic acid molecule of the invention comprises a nucleic acid molecule which is a complement of the nucleotide sequence shown in SEQ ID NO:1 or SEQ ID NO:3 or a portion of either of these nucleotide sequences. A nucleic acid molecule which is complementary to the nucleotide sequence shown in SEQ ID NO:1 or SEQ ID NO:3 is one which is sufficiently complementary to the nucleotide sequence shown in SEQ ID NO:1 or SEQ ID NO:3 such that it can hybridize to the nucleotide sequence shown in SEQ ID NO:1 or SEQ ID NO:3, thereby forming a stable duplex.

In still another preferred embodiment, an isolated nucleic acid molecule of the invention comprises a nucleotide sequence which is at least about 75.5, 76, 77, 78, 79%, preferably at least about 80%, more preferably at least about 85%, even more preferably at least about 90%, and most preferably at least about 95% or more homologous to the nucleotide sequence shown in SEQ ID NO:1 or a portion thereof. In still other particularly preferred embodiments, an isolated nucleic acid molecule of the invention comprises a nucleotide sequence which is at least about 65%, preferably at least about 70%, more preferably at least about 75%, even more preferably at least about 80%, still more preferably at least about 85%, yet more preferably at least about 90%, and most preferably at least about 95% or more homologous to the nucleotide sequence shown in SEQ ID NO:3 or a portion thereof. In additional preferred embodiments, an isolated nucleic acid molecule of the invention comprises a nucleotide sequence which hybridizes, e.g., hybridizes under stringent conditions, to the nucleotide sequence shown in SEQ ID NO:1, SEQ ID NO:3, or a portion of either of these nucleotide sequences.

Moreover, the nucleic acid molecule of the invention can comprise only a portion of the coding region of SEQ ID NO:1 or SEQ ID NO:3, for example a fragment which can be used as a probe or primer or a fragment encoding a biologically active portion of Siva. The nucleotide sequence determined from the cloning of the Siva gene from a mammal allows for the generation of probes and primers designed for use in identifying and/or cloning Siva homologues in other cell types, e.g. from other tissues, as well as Siva homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of SEQ ID NO:1 or SEQ ID NO:3 sense, an anti-sense sequence of SEQ ID NO:1 or SEQ ID NO:3, or naturally-occurring mutants thereof. Primers based on the nucleotide sequence in SEQ ID NO:1 or SEQ ID NO:3 can be used in PCR reactions to clone Siva homologues. Probes based on the Siva nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissue which misexpress a Siva protein, such as by measuring a level of a Siva-encoding nucleic acid in a sample of cells from a subject e.g., detecting Siva mRNA levels or determining whether a genomic Siva gene has been mutated or deleted.

In one embodiment, the nucleic acid molecule of the invention encodes a protein or portion thereof which includes an amino acid sequence which is sufficiently homologous to an amino acid sequence of SEQ ID NO:2 or SEQ ID NO:4 such that the protein or portion thereof maintains the ability to modulate apoptosis, e.g., apoptosis of an immune cell. As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO:2 or SEQ ID NO:4) amino acid residues to an amino acid sequence of SEQ ID NO:2 or SEQ ID NO:4 such that the protein or portion thereof has at least one Siva biological activity, e.g., is able to modulate apoptosis, e.g., apoptosis of an immune cell., e.g., CD27-mediated apoptosis of an immune cell.

Portions of proteins encoded by the Siva nucleic acid molecule of the invention are preferably biologically active portions of the Siva protein. As used herein, the term "biologically active portion of Siva" is intended to include a portion, e.g., a domain/motif, of Siva that has one or more of the following biological activities: 1) it can interact with (e.g., bind to) CD27, e.g., the cytoplasmic tail of CD27; 2) it can modulate the activity of CD27; and 3) it can modulate or regulate apoptosis, e.g., apoptosis of immune cells. In a preferred embodiment of the invention, the portion of the Siva protein is capable of modulating CD27-mediated apoptosis of cells, e.g., immune cells. Standard binding assays, e.g., immunoprecipitations and yeast two-hybrid assays as described herein, can be performed to determine the ability of a Siva protein or a biologically active portion thereof to interact with (e.g., bind to) CD27 or a portion thereof. To determine whether a Siva protein or a biologically active portion thereof can modulate the activity of CD27 and/or modulate apoptosis, immune cells which express CD27 can be transformed with nucleic acid encoding Siva such that Siva is overexpressed. Cell death can then be measured and compared to cell death in control cells. An increase in cell death in the cells which overexpress Siva as compared to the control cells is evidence that Siva modulates CD27 activity. An example of such a test is described in Example V.

In one embodiment, the biologically active portion of Siva comprises a domain or motif, e.g., a domain or motif which has a Siva biological activity described herein. The domain or motif can be a death domain homology region, a zinc finger domain, or a B-Box like ring finger domain or a combination thereof, e.g., a CD27-binding domain. If the biologically active portion is derived from Siva-1, the death domain homology region is preferably at least about 50%, more preferably at least about 60%, still more preferably at least about 70%, yet more preferably at least about 80%, and most preferably at least about 90% or more homologous to the amino acid sequence of SEQ ID NO:7, the zinc finger domain is preferably at least about 50%, more preferably at least about 60%, still more preferably at least about 70%, yet more preferably at least about 80%, and most preferably at least about 90% or more homologous to the amino acid sequence of SEQ ID NO:8; and the B-Box like ring finger domain is preferably at least about 50%, more preferably at least about 60%, still more preferably at least about 70%, yet more preferably at least about 80%, and most preferably at least about 90% or more homologous to the amino acid sequence of SEQ ID NO:9. In a preferred embodiment, the biologically active portion comprises the death domain homology region of Siva-1 as shown in SEQ ID NO:7. In another preferred embodiment, the biologically active portion comprises the zinc finger domain of Siva-1 as shown in SEQ ID NO:8. In yet another preferred embodiment, the biologically active portion comprises the B-Box like ring finger domain of Siva-1 as shown in SEQ ID NO:9.

If the biologically active portion is derived from Siva-2, the death domain homology region is preferably at least about 50%, more preferably at least about 60%, still more preferably at least about 70%, yet more preferably at least about 80%, and most preferably at least about 90% or more homologous to the amino acid sequence of SEQ ID NO:10, the zinc finger domain is preferably at least about 50%, more preferably at least about 60%, still more preferably at least about 70%, yet more preferably at least about 80%, and most preferably at least about 90% or more homologous to the amino acid sequence of SEQ ID NO:11; and the B-Box like ring finger domain is preferably at least about 50%, more preferably at least about 60%, still more preferably at least about 70%, yet more preferably at least about 80%, and most preferably at least about 90% or more homologous to the amino acid sequence of SEQ ID NO:12. In a preferred embodiment, the biologically active portion comprises the death domain homology region of Siva-2 as shown in SEQ ID NO:10. In another preferred embodiment, the biologically active portion comprises the zinc finger domain of Siva-2 as shown in SEQ ID NO:11. In yet another preferred embodiment, the biologically active portion comprises the B-Box like ring finger domain of Siva-2 as shown in SEQ ID NO:12 Additional nucleic acid fragments encoding biologically active portions of Siva can be prepared by isolating a portion of SEQ ID NO:1 or SEQ ID NO:3, expressing the encoded portion of Siva protein or peptide (e.g., by recombinant expression in vitro) and assessing the activity of the encoded portion of Siva protein or peptide.

The invention further encompasses nucleic acid molecules that differ from the nucleotide sequence shown in SEQ ID NO:1 or SEQ ID NO:3 (and portions thereof) due to degeneracy of the genetic code and thus encode the same Siva protein as that encoded by the nucleotide sequence shown in SEQ ID NO:1 or SEQ ID NO:3. In another embodiment, an isolated nucleic acid molecule of the invention has a nucleotide sequence encoding a protein having an amino acid sequence shown in SEQ ID NO:2 or SEQ ID NO:4.

In addition to the human Siva nucleotide sequences shown in SEQ ID NO:1 and SEQ ID NO:3, it will be appreciated by those skilled in the art that DNA sequence polymorphisms that lead to changes in the amino acid sequences of Siva may exist within a population (e.g., the human population). Such genetic polymorphism in the Siva gene may exist among individuals within a population due to natural allelic variation. As used herein, the terms "gene" and "recombinant gene" refer to nucleic acid molecules comprising an open reading frame encoding a Siva protein, preferably a mammalian Siva protein. Such natural allelic variations can typically result in 1–5% variance in the nucleotide sequence of the Siva gene. Any and all such nucleotide variations and resulting amino acid polymorphisms in Siva that are the result of natural allelic variation and that do not alter the functional activity of Siva are intended to be within the scope of the invention. Moreover, nucleic acid molecules encoding Siva proteins from other species, and thus which have a nucleotide sequence which differs from the human sequence of SEQ ID NO:1 or SEQ ID NO:3, are intended to be within the scope of the invention. Nucleic acid molecules corresponding to natural allelic variants and nonhuman homologues of the human Siva cDNA of the invention can be isolated based on their homology to the human Siva nucleic acid disclosed herein using the human cDNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1 or SEQ ID NO:3. In other embodiments, the nucleic acid is at least 30, 50, 100, 250 or 500 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1 or SEQ ID NO:3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural human Siva.

In addition to naturally-occurring allelic variants of the Siva sequence that may exist in the population, the skilled artisan will further appreciate that changes can be introduced by mutation into the nucleotide sequence of SEQ ID NO:1 or SEQ ID NO:3, thereby leading to changes in the amino acid sequence of the encoded Siva protein, without altering the functional ability of the Siva protein. For example, nucleotide substitutions leading to amino acid substitutions at "non-essential" amino acid residues can be made in the sequence of SEQ ID NO:1 or SEQ ID NO:3. A "non-essential" amino acid residue is a residue that can be altered from the wild-type sequence of Siva (e.g., the sequence of SEQ ID NO:2 or SEQ ID NO:4) without altering the activity of Siva, whereas an "essential" amino acid residue is required for Siva activity. For example, conserved amino acid residues, e.g., cysteines, in the B-Box like ring finger domain and zinc finger domain of Siva are most likely important for binding to CD27 proteins and thus may be essential residues of Siva. Other amino acid residues, however, (e.g., those that are not conserved or only semi-conserved in the domains of Siva described herein) may not be essential for activity and thus are likely to be amenable to alteration without altering Siva activity.

Accordingly, another aspect of the invention pertains to nucleic acid molecules encoding Siva proteins that contain changes in amino acid residues that are not essential for Siva activity. Such Siva proteins differ in amino acid sequence from SEQ ID NO:2 or SEQ ID NO:4 yet retain at least one of the Siva activities described herein. In one embodiment, the isolated nucleic acid molecule comprises a nucleotide sequence encoding a Siva-1 protein, wherein the Siva-1 protein comprises an amino acid sequence at least about 71, 72, 73, 74, 75, 76, 77, 78, 79%, preferably at least about 80%, more preferably at least about 85%, and even more preferably at least about 90%, and most preferably at least about 95% or more homologous to the amino acid sequence of SEQ ID NO:2 (e.g., the entire amino acid sequence of SEQ ID NO:2) and is capable of modulating apoptosis, e.g., apoptosis of an immune cell. In another embodiment, the nucleic acid molecule comprises a nucleotide sequence encoding a Siva-2 protein, wherein the Siva-2 protein comprises an amino acid sequence which is at least about 65%, preferably at least about 70%, more preferably at least about 75%, even more preferably at least about 80%, still more preferably at least about 90%, and most preferably at least about 95% or more homologous to the nucleotide sequence shown in SEQ ID NO:4 (e.g., the entire amino acid sequence of SEQ ID NO:4) and is capable of modulating apoptosis, e.g., apoptosis of an immune cell.

To determine the percent homology of two amino acid sequences (e.g., SEQ ID NO:2 and a mutant form thereof or SEQ ID NO:4 or a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence is occupied by the same amino acid residue or nucleotide as the corresponding position in the other sequence (e.g., a mutant form of Siva), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

An isolated nucleic acid molecule encoding a Siva protein homologous to the protein of SEQ ID NO:2 or SEQ ID NO:4 can be created by introducing one or more nucleotide substitutions, additions or deletions into the nucleotide sequence of SEQ ID NO:1 or SEQ ID NO:3, respectively, such that one or more amino acid substitutions, additions or deletions are introduced into the encoded protein. Mutations can be introduced into SEQ ID NO:1 or SEQ ID NO:3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cystcine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in Siva is preferably replaced with another amino acid residue from the same side chain family. Alternatively, in another embodiment, mutations can be introduced randomly along all or part of a Siva coding sequence, such as by saturation mutagenesis, and the resultant mutants can be screened for a Siva activity described herein to identify mutants that retain Siva activity. Following mutagenesis of SEQ ID NO:1 or SEQ ID NO:3, the encoded protein can be expressed recombinantly (e.g., as described in Example IV) and the activity of the protein can be determined using, for example, assays described herein.

In addition to the nucleic acid molecules encoding Siva proteins described above, another aspect of the invention pertains to isolated nucleic acid molecules which are anti-sense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire Siva coding strand, or to only a portion thereof. In one embodiment, an antisense nucleic acid molecule is antisense to a "coding region" of the coding strand of a nucleotide sequence encoding Siva. The term "coding region" refers to the region of the nucleotide sequence comprising codons which are translated into amino acid residues (e.g., the entire coding region of SEQ ID NO:1 comprises nucleotides 133 to 699, the entire coding region of SEQ ID NO:3 comprises nucleotides 133 to 504). In another embodiment, the antisense nucleic acid molecule is antisense to a "noncoding region" of the coding strand of a nucleotide sequence encoding Siva. The term "noncoding region" refers to 5' and 3' sequences which flank the coding region that are not translated into amino acids (i.e., also referred to as 5' and 3' untranslated regions).

Given the coding strand sequences encoding Siva disclosed herein (e.g., SEQ ID NO:1, SEQ ID NO:3), antisense nucleic acids of the invention can be designed according to the rules of Watson and Crick base pairing. The antisense nucleic acid molecule can be complementary to the entire coding region of Siva mRNA, but more preferably is an oligonucleotide which is antisense to only a portion of the coding or noncoding region of Siva mRNA. For example, the antisense oligonucleotide can be complementary to the region surrounding the translation start site of Siva mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally-occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an Siva protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave Siva mRNA transcripts to thereby inhibit translation of Siva mRNA. A ribozyme having specificity for a Siva-encoding nucleic acid can be designed based upon the nucleotide sequence of a Siva cDNA disclosed herein (i.e., SEQ ID NO:1 and SEQ ID NO:3). For example, a derivative of a Tetrahymena L-19 IVS RNA can be constructed in which the nucleotide sequence of the active site is complementary to the nucleotide sequence to be cleaved in a Siva-encoding mRNA. See, e.g., Cech et al. U.S. Pat. No. 4,987,071 and Cech et al. U.S. Pat. No. 5,116,742. Alternatively, Siva mRNA can be used to select a catalytic RNA having a specific ribonuclease activity from a pool of RNA molecules. See, e.g., Bartel, D. and Szostak, J. W. (1993) *Science* 261:1411–1418.

Alternatively, Siva gene expression can be inhibited by targeting nucleotide sequences complementary to the regulatory region of the Siva (e.g., the Siva promoter and/or enhancers) to form triple helical structures that prevent transcription of the Siva gene in target cells. See generally, Helene, C. (1991) *Anticancer Drug Des.* 6(6):569–84; Helene, C. et al. (1992) *Ann. N. Y Acad. Sci.* 660:27–36; and Maher, L. J. (1992) *Bioassays* 14(12):807–15.

II. Recombinant Expression Vectors and Host Cells

Another aspect of the invention pertains to vectors, preferably expression vectors, containing a nucleic acid encoding Siva (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology. Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., Siva proteins, mutant forms of Siva, fusion proteins, etc.).

The recombinant expression vectors of the invention can be designed for expression of Siva in prokaryotic or eukaryotic cells. For example, Siva can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the Siva is cloned into a pGEX expression vector to create a vector encoding a fusion protein comprising, from the N-terminus to the C-terminus, GST-thrombin cleavage site-Siva. The fusion protein can be purified by affinity chromatography using glutathione-agarose resin. Recombinant Siva unfused to GST can be recovered by cleavage of the fusion protein with thrombin.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology. Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the Siva expression vector is a yeast expression vector. Examples of vectors for expression in yeast *S. cerivisae* include pYepSec1 (Baldari, et al., (1987) *Embo J*. 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Alternatively, Siva can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J*. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning. A Laboratory Manual*. 2nd, ed., *Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev*. 1:268–277), lymphoid-specific promoters (Calame and Eaton (1988) *Adv. Immunol*. 43:235–275), in particular promoters of T cell receptors (Winoto and Baltimore (1989) *EMBO J*. 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev*. 3 :537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to Siva mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, HI. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, Siva protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual*. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding Siva or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) Siva protein. Accordingly, the invention further provides methods for producing Siva protein using the host cells of the invention. In one embodiment, the method comprises culturing the host cell of invention (into which a recombinant expression vector encoding Siva has been introduced) in a suitable medium until Siva is produced. In another embodiment, the method further comprises isolating Siva from the medium or the host cell.

The host cells of the invention can also be used to produce nonhuman transgenic animals. The nonhuman transgenic animals can be used in screening assays designed to identify agents or compounds, e.g., drugs, phanrnaceuticals, etc., which are capable of ameliorating detrimental symptoms of selected disorders such as proliferative disorders and autoimmune diseases. For example, in one embodiment, a host cell of the invention is a fertilized oocyte or an embryonic stem cell into which Siva-coding sequences have been introduced. Such host cells can then be used to create non-human transgenic animals in which exogenous Siva sequences have been introduced into their genome or homologous recombinant animals in which endogenous Siva sequences have been altered. Such animals are useful for studying the function and/or activity of Siva and for identifying and/or evaluating modulators of Siva activity. As used herein, a "transgenic animal" is a nonhuman animal, preferably a mammal, more preferably a rodent such as a rat or mouse, in which one or more of the cells of the animal includes a transgcne. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous Siva gene has been altered by homologous recombination between the endogenous gene and an exogenous DNA molecule introduced into a cell of the animal, e.g., an embryonic cell of the animal, prior to development of the animal.

A transgenic animal of the invention can be created by introducing Siva-encoding nucleic acid into the male pronuclei of a fertilized oocyte, e.g., by microinjection, retroviral infection, and allowing the oocyte to develop in a pseudopregnant female foster animal. The human Siva cDNA sequence of SEQ ID NO:1 or SEQ ID NO:3 can be introduced as a transgene into the genome of a nonhuman animal. Alternatively, a nonhuman homologue of the human Siva gene can be isolated based on hybridization to the human Siva cDNA (described further in subsection I above) and used as a transgene. Intronic sequences and polyadenylation signals can also be included in the transgene to increase the efficiency of expression of the transgene. A tissue-specific regulatory sequence(s) can be operably linked to the Siva transgene to direct expression of Siva protein to particular cells. Methods for generating transgenic animals via embryo manipulation and microinjection, particularly animals such as mice, have become conventional in the art and are described, for example, in U.S. Pat. Nos. 4,736.866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the Siva transgene in its genome and/or expression of Siva mRNA in tissues or cells of the animals. A transgenic founder animal can then be used to breed additional animals carrying the transgene. Moreover, transgenic animals carrying a transgene encoding Siva can further be bred to other transgenic animals carrying other transgenes.

To create a homologous recombinant animal, a vector is prepared which contains at least a portion of a Siva gene into which a deletion, addition or substitution has been introduced to thereby alter, e.g., functionally disrupt, the Siva gene. The Siva gene can be a human gene (e.g., from a human genomic clone isolated from a human genomic library screened with the cDNA of SEQ ID NO:1 or SEQ ID NO:3), but more preferably, is a nonhuman homologue of a human Siva gene. For example, a nonhuman homologue of the human Siva gene can be isolated from a relevant genomic DNA library using the human Siva cDNA of SEQ ID NO:1 or SEQ ID NO:3 as a probe. The nonhuman homologue Siva gene then can be used to construct a homologous recombination vector suitable for altering an endogenous Siva gene in the genome of nonhuman animal from which the Siva gene is derived. In a preferred embodiment, the vector is designed such that, upon homologous recombination, the endogenous Siva gene is functionally disrupted (i.e., no longer encodes a functional protein; also referred to as a "knock out" vector). Alternatively, the vector can be designed such that, upon homologous recombination, the endogenous Siva gene is mutated or otherwise altered but still encodes functional protein (e.g., the upstream regulatory region can be altered to thereby alter the expression of the endogenous Siva protein). In the homologous recombination vector, the altered portion of the Siva gene is flanked at its 5' and 3' ends by additional nucleic acid of the Siva gene to allow for homologous recombination to occur between the exogenous Siva gene carried by the vector and an endogenous Siva gene in an embryonic stem cell. The additional flanking Siva nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced Siva gene has homologously recombined with the endogenous Siva gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhumans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

III. Isolated Siva Proteins and Anti-Siva Antibodies

Another aspect of the invention pertains to isolated Siva proteins, and biologically active portions thereof, as well as peptide fragments suitable for use as immunogens to raise anti-Siva antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of Siva protein in which the protein is separated from cellular components of the cells in which it is naturally or recombinantly produced. In one embodiment, the language "substantially free of cellular material" includes preparations of Siva protein having less than about 30% (by dry weight) of non-Siva protein (also referred to herein as a "contaminating protein"), more preferably less than about 20% of non-Siva protein, still more preferably less than about 10% of non-Siva protein, and most preferably less than about 5% non-Siva protein. When the Siva protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of Siva protein in which the protein is separated from chemical precursors or other chemicals which are involved in the synthesis of the protein. In one embodiment, the language "substantially free of chemical precursors or other chemicals" includes preparations of Siva protein having less than about 30% (by dry weight) of chemical precursors or non-Siva chemicals, more preferably less than about 20% chemical precursors or non-Siva chemicals, still more preferably less than about 10% chemical precursors or non-Siva chemicals, and most preferably less than about 5% chemical precursors or non-Siva chemicals. In preferred embodiments, isolated proteins or biologically active portions thereof lack contaminating proteins from the same animal from which the Siva protein is derived. Typically, such proteins are produced by recombinant expression of, for example, a human Siva protein in a nonhuman cell.

An isolated Siva protein or a portion thereof of the invention can modulate apoptosis, e.g., apoptosis of an immune cell. In preferred embodiments, the protein or portion thereof comprises an amino acid sequence which is sufficiently homologous to an amino acid sequence of SEQ ID NO:2 or SE.Q ID NO:4 such that the protein or portion thereof maintains the ability to modulate apoptosis, e.g., apoptosis of an immune cell. The portion of the protein is preferably a biologically active portion as described herein. In another preferred embodiment, the Siva protein (i.e., amino acid residues 1–189 of the Siva-1 protein) has an amino acid sequence shown in SEQ ID NO:2. In yet another preferred embodiment, the Siva protein (i.e., amino acid residues 1 to 124 of the Siva-2 protein) has an amino acid sequence shown in SEQ ID NO:4. In yet another preferred embodiment, the Siva protein has an amino acid sequence which is encoded by a nucleotide sequence which hybridizes, e.g., hybridizes under stringent conditions, to the nucleotide sequence of SEQ ID NO:1 or SEQ ID NO:3. In still another preferred embodiment, the Siva protein has an amino acid sequence which is encoded by a nucleotide sequence which is at least about 75.5, 76, 77, 78, 79%, preferably at least about 80%, more preferably at least about 85%, still more preferably at least about 90%, and most preferably at least about 95% or more homologous to the nucleotide sequence shown in SEQ ID NO:1. In still another particularly preferred embodiments, the Siva protein has an amino acid sequence which is encoded by a nucleotide sequence which is at least about 65%, preferably at least about 70%, more preferably at least about 75%, even more preferably at least about 80%, still more preferably at least about 85%, yet more preferably at least about 90%, and most preferably at least about 95% or more homologous to the nucleotide sequence shown in SEQ ID NO:3. The preferred Siva proteins of the present invention also preferably possess at least one of the Siva biological activities described herein.

In other embodiments, the Siva protein is substantially homologous to the amino acid sequence of SEQ ID NO:2 or SEQ ID NO:4 and retains the functional activity of the protein of SEQ ID NO:2 or SEQ ID NO:4 yet differs in amino acid sequence due to natural allelic variation or mutagenesis, as described in detail in subsection I above.

Biologically active portions of the Siva protein include peptides comprising amino acid sequences derived from the amino acid sequence of the Siva protein, e.g., the amino acid sequence shown in SEQ ID NO:2 or SEQ ID NO:4 or the amino acid sequence of a protein homologous to the Siva protein, which include less amino acids than the full length Siva protein or the full length protein which is homologous to the Siva protein, and exhibit at least one biological activity of the Siva protein. Typically, biologically active portions (peptides, e.g., peptides which are, for example, 5, 10, 15, 20, 30, 35, 36, 37, 38, 39, 40, 50, 100 or more amino acids in length) comprise a domain or motif, e.g., a death domain homology region, a zinc finger domain, or a B-Box like ring finger domain, with at least one activity of the Siva protein. In a preferred embodiment, the death domain homology region comprises the amino acid sequence of SEQ ID NO:7 or SEQ ID NO:9. In another preferred embodiment, the zinc finger domain comprises the amino acid sequence of SEQ ID NO:8 or SEQ ID NO:11. In yet another preferred embodiment, the B-Box like ring finger domain comprises the amino acid sequence of SEQ ID NO:9 or SEQ ID NO:12. Preferably, the preferred biologically active portions of the Siva proteins have one or more of the following biological activities: 1) it is capable of modulating apoptosis, e.g., apoptosis of an immune cells; 2) it can interact with (e.g., bind to) CD27 or a portion thereof, e.g., the cytoplasmic tail of CD27; and 3) it can modulate the activity of CD27. Moreover, other biologically active portions, in which other regions of the protein are deleted, can be prepared by recombinant techniques and evaluated for one or more of the biological activities described herein. Preferably, the biologically active portions of the Siva protein include one or more selected domains/motifs or portions thereof having biological activity.

Siva proteins are preferably produced by recombinant DNA techniques. For example, a nucleic acid molecule encoding the protein is cloned into an expression vector (as described above), the expression vector is introduced into a host cell (as described above) and the Siva protein is expressed in the host cell. The Siva protein can then be isolated from the cells by an appropriate purification scheme using standard protein purification techniques. Alternative to recombinant expression, a Siva protein, polypeptide, or peptide can be synthesized chemically using standard peptide synthesis techniques. Moreover, native Siva protein can be isolated from cells (e.g., peripheral blood lymphocytes), for example using an anti-Siva antibody (described further below).

The invention also provides Siva chimeric or fusion proteins. As used herein, an Siva "chimeric protein" or "fusion protein" comprises a Siva polypeptide operatively linked to a non-Siva polypeptide. A "Siva polypeptide" refers to a polypeptide having an amino acid sequence corresponding to Siva, whereas a "non-Siva polypeptide" refers to a polypeptide having an amino acid sequence corresponding to a protein which is not substantially homologous to the Siva protein, e.g., a protein which is different from the Siva protein and which is derived from the same or a different organism. Within the fusion protein, the term "operatively linked" is intended to indicate that the Siva polypeptide and the non-Siva polypeptide are fused in-frame to each other. The non-Siva polypeptide can be fused to the N-terminus or C-terminus of the Siva polypeptide. For example, in one embodiment the fusion protein is a GST-Siva fusion protein in which the Siva sequences are fused to the C-terminus of the GST sequences. Such fusion proteins can facilitate the purification of recombinant Siva. In another embodiment, the fusion protein is a Siva protein containing a heterologous signal sequence at its N-terminus. In certain host cells (e.g., mammalian host cells), expression and/or secretion of Siva can be increased through use of a heterologous signal sequence.

Preferably, a Siva chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A Siva-encoding nucleic acid can be cloned into such an expression vector such that the fusion moiety is linked in-frame to the Siva protein.

The present invention also pertains to homologues of the Siva proteins which function as either a Siva agonist (mimetic) or a Siva antagonist. In a preferred embodiment, the Siva agonists and antagonists stimulate or inhibit, respectively, a subset of the biological activities of the naturally-occurring form of the Siva protein. Thus, specific biological effects can be elicited by treatment with a homologue of limited function. In one embodiment, treatment of a subject with a homologue having a subset of the biological activities of the naturally-occurring form of the protein has fewer side effects in a subject relative to treatment with the naturally-occurring form of the Siva protein.

Homologues of the Siva protein can be generated by mutagenesis, e.g., discrete point mutation or truncation of the Siva protein. As used herein, the term "homologue" refers to a variant form of the Siva protein which acts as an agonist or antagonist of the activity of the Siva protein. An agonist of the Siva protein can retain substantially the same, or a subset, of the biological activities of the Siva protein. An antagonist of the Siva protein can inhibit one or more of the activities of the naturally-occurring form of the Siva protein, by, for example, competitively binding to a downstream or upstream member of the Siva cascade which includes the Siva protein. Thus, the mammalian Siva protein and homologues thereof of the present invention can be either positive or negative regulators of apoptosis, e.g., apoptosis of an immune cell.

In an alternative embodiment, homologues of the Siva protein can be identified by screening combinatorial libraries of mutants, e.g., truncation mutants, of the Siva protein for Siva protein agonist or antagonist activity. In one embodiment, a variegated library of Siva variants is generated by combinatorial mutagenesis at the nucleic acid level and is encoded by a variegated gene library. A variegated library of Siva variants can be produced by, for example, enzymatically ligating a mixture of synthetic oligonucleotides into gene sequences such that a degenerate set of potential Siva sequences is expressible as individual polypeptides, or alternatively, as a set of larger fusion proteins (e.g., for phage display) containing the set of Siva sequences therein. There are a variety of methods which can be used to produce libraries of potential Siva homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Siva sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the Siva coding region can be used to generate a variegated population of Siva fragments for screening and subsequent selection of homologues of an Siva protein. In one embodiment, a library of coding sequence fragments can be generated by treating a double stranded PCR fragment of an Siva coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the Siva protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Siva homologues. The most widely used techniques, which are amenable to high through-put analysis. for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify Siva homologues (Arkin and Yourvan (1992) *PNAS* 89:7811–7815; Delgrave et al. (1993) *Protein Engineering* 6(3):327–331).

An isolated Siva protein, or a portion or fragment thereof, can be used as an immunogen to generate antibodies that bind Siva using standard techniques for polyclonal and monoclonal antibody preparation. The full-length Siva protein can be used or, alternatively, the invention provides antigenic peptide fragments of Siva for use as immunogens.

The antigenic peptide of Siva comprises at least 8 amino acid residues of the amino acid sequence shown in SEQ ID NO:2 or SEQ ID NO:4 and encompasses an epitope of Siva such that an antibody raised against the peptide forms a specific immune complex with Siva. Preferably, the antigenic peptide comprises at least 10 amino acid residues, more preferably at least 15 amino acid residues, even more preferably at least 20 amino acid residues, and most preferably at least 30 amino acid residues. An example of an antigenic Siva peptide is the peptide which includes amino acid residues 40 to 73 of SEQ ID NO:2. This peptide was coupled to KLH and used to raise polyclonal anti-Siva antibodies in mice. Other preferred epitopes encompassed by the antigenic peptide are regions of Siva that are located on the surface of the protein, e.g., hydrophilic regions.

A Siva immunogen typically is used to prepare antibodies by immunizing a suitable subject, (e.g., rabbit, goat, mouse or other mammal) with the immunogen. An appropriate immunogenic preparation can contain, for example, recombinantly expressed Siva protein or a chemically synthesized Siva peptide. The preparation can further include an adjuvant, such as Freund's complete or incomplete adjuvant, or similar immunostimulatory agent. Immunization of a suitable subject with an immunogenic Siva preparation induces a polyclonal anti-Siva antibody response.

Accordingly, another aspect of the invention pertains to anti-Siva antibodies. The term "antibody" as used herein refers to immunoglobulin molecules and immunologically active portions of immunoglobulin molecules, i.e., molecules that contain an antigen binding site which specifically binds (immunoreacts with) an antigen, such as Siva. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind Siva. The term "monoclonal antibody" or "monoclonal antibody composition", as used herein, refers to a population of antibody molecules that contain only one species of an antigen binding site capable of immunoreacting with a particular epitope of Siva. A monoclonal antibody composition thus typically displays a single binding affinity for a particular Siva protein with which it immunoreacts.

Polyclonal anti-Siva antibodies can be prepared as described above by immunizing a suitable subject with a Siva immunogen. The anti-Siva antibody titer in the immunized subject can be monitored over time by standard techniques, such as with an enzyme linked immunosorbent assay (ELISA) using immobilized Siva. If desired, the antibody molecules directed against Siva can be isolated from the mammal (e.g., from the blood) and further purified by well known techniques, such as protein A chromatography to obtain the IgG fraction. At an appropriate time after immunization, e.g., when the anti-Siva antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet*. 3:231–36). Briefly, an immortal cell line (typically a myeloma) is fused to lymphocytes (typically splenocytes) from a mammal immunized with a Siva immunogen as described above, and the culture supernatants of the resulting hybridoma cells are screened to identify a hybridoma producing a monoclonal antibody that binds Siva.

Any of the many well known protocols used for fusing lymphocytes and immortalized cell lines can be applied for the purpose of generating an anti-Siva monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse mycloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind Siva, e.g., using a standard ELISA assay.

Alternative to preparing monoclonal antibody-secreting hybridomas, a monoclonal anti-Siva antibody can be identified and isolated by screening a recombinant combinatorial immunoglobulin library (e.g., an antibody phage display library) with Siva to thereby isolate immunoglobulin library members that bind Siva. Kits for generating and screening phage display libraries are commercially available (e.g., the Pharmacia *Recombinant Phage Antibody System*, Catalog No. 27-9400-01; and the Stratagene *SurfZAP*™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.*

226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc. Acid Res.* 19:4133–4137; Barbas et al. (1991) *PNAS* 88:7978–7982; and McCafferty et al. *Nature* (1990) 348:552–554.

Additionally, recombinant anti-Siva antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218, Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:141:4053–4060; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-Siva antibody (e.g., monoclonal antibody) can be used to isolate Siva by standard techniques, such as affinity chromatography or immunoprecipitation. An anti-Siva antibody can facilitate the purification of natural Siva from cells and of recombinantly produced Siva expressed in host cells. Moreover, an anti-Siva antibody can be used to detect Siva protein (e.g., in a cellular lysate or cell supernatant) in order to evaluate the abundance and pattern of expression of the Siva protein. Anti-Siva antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

IV. Pharmaceutical Compositions

The Siva nucleic acid molecules, Siva proteins, Siva modulators, and anti-Siva antibodies (also referred to herein as "active compounds") of the invention can be incorporated into pharmaceutical compositions suitable for administration to a subject, e.g., a human. Such compositions typically comprise the nucleic acid molecule, protein, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a Siva protein or anti-Siva antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, polypeptides, polypeptide homologues, modulators, and antibodies described herein can be used in one or more of the following methods: 1) drug screening assays; 2) diagnostic assays; and 3) methods of treatment. A Siva protein of the invention has one or more of the activities described herein and can thus be used to, for example, modulate apoptosis, e.g., apoptosis of an immune cell. The isolated nucleic acid molecules of the invention can be used to express Siva protein (e.g., via a recombinant expression vector in a host cell in gene therapy applications), to detect Siva mRNA (e.g., in a biological sample) or a genetic lesion in a Siva gene, and to modulate Siva activity, as described further below. In addition, the Siva proteins can be used to screen drugs or compounds which modulate Siva protein activity as well as to treat disorders characterized by insufficient production of Siva protein or production of Siva protein forms which have decreased activity compared to wild type Siva. Moreover, the anti-Siva antibodies of the invention can be used to detect and isolate Siva protein and modulate Siva protein activity.

a. Drug Screening Assays:

The invention provides methods for identifying compounds or agents which can be used to treat disorders characterized by (or associated with) aberrant or abnormal Siva nucleic acid expression and/or Siva protein activity. These methods are also referred to herein as drug screening assays and typically include the step of screening a candidate/test compound or agent for the ability to interact with (e.g., bind to) a Siva protein, to modulate the interaction of a Siva protein and a target molecule, and/or to modulate Siva nucleic acid expression and/or Siva protein activity. Candidate/test compounds or agents (e.g., candidate/test compounds which can restore or replace normal cell function/morphology in cells containing aberrant or abnormal Siva nucleic acid expression and/or Siva protein activity, candidate/test compounds that can bypass Siva functions) which have one or more of these abilities can be used as drugs to treat disorders characterized by aberrant or abnormal Siva nucleic acid expression and/or Siva protein activity. Candidate/test compounds include, for example, 1) peptides such as soluble peptides, including Ig-tailed fusion peptides and members of random peptide libraries (see, e.g., Lam, K. S. et al. (1991) *Nature* 354:82–84; Houghten, R. et al. (1991) *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

In one embodiment, the invention provides assays for screening candidate/test compounds which interact with (e.g., bind to) Siva protein. Typically, the assays are cell-free assays which include the steps of combining a Siva protein or a biologically active portion thereof, and a candidate/test compound, e.g., under conditions which allow for interaction of (e.g., binding of) the candidate/test compound to the Siva protein or portion thereof to form a complex, and detecting the formation of a complex, in which the ability of the candidate compound to interact with (e.g., bind to) the Siva protein or fragment thereof is indicated by the presence of the candidate compound in the complex. Formation of complexes between the Siva protein and the candidate compound can be quantitated, for example, using standard immunoassays.

In another embodiment, the invention provides screening assays to identify candidate/test compounds which modulate (e.g., stimulate or inhibit) the interaction (and most likely Siva activity as well) between a Siva protein and a molecule (target molecule) with which the Siva protein normally interacts. An example of such a target molecule includes CD27 or a portion thereof, e.g., a cytoplasmic domain of CD27 and other proteins which may function upstream (including both stimulators and inhibitors of activity) or downstream of the Siva protein in an apoptosis signaling pathway. Typically, the assays are cell-free assays which include the steps of combining a Siva protein or a biologically active portion thereof, a Siva target molecule (e.g., CD27) and a candidate/test compound, e.g., under conditions wherein but for the presence of the candidate compound, the Siva protein or biologically active portion thereof interacts with (e.g., binds to) the target molecule, and detecting the formation of a complex which includes the Siva protein and the target molecule or detecting the interaction/reaction of the Siva protein and the target molecule. Detection of complex formation can include direct quantitation of the complex by, for example, measuring inductive effects of the Siva protein. A statistically significant change, such as a decrease, in the interaction of Siva and target molecule (e.g., in the formation of a complex between Siva and the target molecule) in the presence of a candidate compound (relative to what is detected in the absence of the candidate compound) is indicative of a modulation (e.g., stimulation or inhibition) of the interaction between the Siva protein and the target molecule. Modulation of the formation of complexes between the Siva protein and the target molecule can be quantitated using, for example, an immunoassay.

To perform the above drug screening assays, it is desirable to immobilize either Siva or its target molecule to facilitate separation of complexes from uncomplexed forms of one or both of the proteins, as well as to accommodate automation of the assay. Interaction (e.g., binding of) of Siva to a target molecule, in the presence and absence of a candidate compound, can be accomplished in any vessel suitable for containing the reactants. Examples of such vessels include microtitre plates, test tubes, and micro-centrifuge tubes. In one embodiment, a fusion polypeptide can be provided which adds a domain that allows the polypeptide to be bound to a matrix. For example, glutathione-S-transferase/Siva fusion polypeptides can be adsorbed onto glutathione sepharose beads (Sigma Chemical, St. Louis, Mo.) or glutathione derivatized microtitre plates, which are then combined with the cell lysates (e.g. $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of Siva-binding polypeptide found in the bead fraction quantitated from the gel using standard electrophoretic techniques.

Other techniques for immobilizing polypeptides on matrices can also be used in the drug screening assays of the invention. For example, either Siva or its target molecule can be immobilized utilizing conjugation of biotin and streptavidin. Biotinylated Siva molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with Siva but which do not interfere with binding of the polypeptide to its target molecule can be derivatized to the wells of the plate, and Siva trapped in the wells by antibody conjugation. As described above, preparations of a Siva-binding polypeptide and a candidate compound are incubated in the Siva-presenting wells of the plate, and the amount of complex trapped in the well can be quantitated. Methods for detecting such complexes, in addition to those described above for the GST-immobilized complexes, include immunodetection of complexes using antibodies reactive with the Siva target molecule, or which are reactive with Siva polypeptide and compete with the target molecule; as well as enzyme-linked assays which rely on detecting an enzymatic activity associated with the target molecule.

In yet another embodiment, the invention provides a method for identifying a compound (e.g., a screening assay) capable of use in the treatment of a disorder characterized by (or associated with) aberrant or abnormal Siva nucleic acid expression or Siva protein activity. T his method typically includes the step of assaying the ability of the compound or agent to modulate the expression of the Siva nucleic acid or the activity of the Siva protein thereby identifying a compound for treating a disorder characterized by aberrant or abnormal Siva nucleic acid expression or Siva protein activity. Disorders characterized by aberrant or abnormal Siva nucleic acid expression or Siva protein activity are described herein. Methods for assaying the ability of the compound or agent to modulate the expression of the Siva nucleic acid or activity of the Siva protein are typically cell-based assays. For example, cells which are sensitive to ligands which transduce signals via a pathway involving Siva can be induced to overexpress a Siva protein in the presence and absence of a candidate compound. Candidate compounds which produce a statistically significant change in Siva-dependent responses (either stimulation or inhibition) can be identified. In one embodiment, expression of the Siva nucleic acid or activity of Siva protein is modulated in cells and the effects of candidate compounds on the readout of interest (such as rate of cell proliferation, differentiation, death) are measured. For example, the expression of genes which are up- or down-regulated in response to a Siva-dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected. Phosphorylation of Siva or Siva target molecules can also be measured, for example, by immunoblotting.

Alternatively, modulators of Siva expression (e.g., compounds which can be used to treat a disorder characterized by aberrant or abnormal Siva nucleic acid expression or Siva protein activity) can be identified in a method wherein a cell is contacted with a candidate compound and the expression of Siva mRNA or protein in the cell is determined. The level of expression of Siva mRNA or protein in the presence of the candidate compound is compared to the level of expression of Siva mRNA or polypeptide in the absence of the candidate compound. The candidate compound can then be identified as a modulator of Siva nucleic acid expression based on this comparison and be used to treat a disorder characterized by aberrant Siva nucleic acid expression. For example, when expression of Siva mRNA or polypeptide is greater (statistically significantly greater) in the presence of the candidate compound than in its absence, the candidate compound is identified as a stimulator of Siva nucleic acid expression. Alternatively, when Siva nucleic acid expression is less (statistically significantly less) in the presence of the candidate compound than in its absence, the candidate compound is identified as an inhibitor of Siva nucleic acid expression. The level of Siva nucleic acid expression in the cells can be determined by methods described herein for detecting Siva mRNA or protein.

In yet another aspect of the invention, the Siva proteins can be used as "bait proteins" in a two-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biolechniques* 14:920–924; Iwabuchi et al. (1993) *Oncogene* 8:1693–1696; and Brent WO 94/10300), to identify other proteins, which bind to or interact with Siva ("Siva-binding proteins" or "Siva-bp") and modulate Siva protein activity. Such Siva-binding proteins are also likely to be involved in the propagation of signals by the Siva protein as, for example, upstream or downstream elements of the Siva pathway.

The two-hybrid system is based on the modular nature of most transcription factors. which consist of separable DNA-binding and activation domains. Bartel, P. et al. "Using the Two-Hybrid System to Detect Protein-Protein Interactions" in Cellular Interactions in Development: A Practical Approach, Hartley, D. A. ed. (Oxford University Press, Oxford, 1993) pp. 153–179. Briefly, the assay utilizes two different DNA constructs. In one construct, the gene that codes for Siva is fused to a gene encoding the DNA binding domain of a known transcription factor (e.g., GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" proteins are able to interact, in vivo, forming a Siva-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with Siva.

Modulators of Siva protein activity and/or Siva nucleic acid expression identified according to these drug screening assays can be used to treat, for example, proliferative disorders, e.g., proliferative disorders of immune cells and autoimmune diseases. These methods of treatment include the steps of administering the modulators of Siva protein activity and/or nucleic acid expression, e.g., in a pharmaceutical composition as described in subsection IV above, to a subject in need of such treatment, e.g., a subject with a disorder described herein.

b. Diagnostic Assays:

The invention further provides methods for detecting the presence of Siva in a biological sample. These methods involve contacting the biological sample with a compound or an agent capable of detecting Siva protein or mRNA. A preferred agent for detecting Siva mRNA is a labeled or labelable nucleic acid probe capable of hybridizing to Siva mRNA. The nucleic acid probe can be, for example, the full-length Siva cDNA of SEQ ID NO:1 or SEQ ID NO:3, or a portion thereof, such as an oligonucleotide of at least 15, 30, 50, 100, 250 or 500 nucleotides in length and sufficient to specifically hybridize under stringent conditions to Siva mRNA. A preferred agent for detecting Siva protein is a labeled or labelable antibody capable of binding to Siva protein. Antibodies can be polyclonal, or more preferably, monoclonal. An intact antibody, or a fragment thereof (e.g., Fab or $F(ab')_2$) can be used. The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect Siva mRNA or polypeptide in a biological sample in vitro as well as in vivo. For example, in vitro techniques for detection of Siva mRNA include Northern hybridizations and in situ hybridizations. In vitro techniques for detection of Siva protein include enzyme linked immunosorbent assays (ELISAs), Western blots, immunoprecipitations and immunofluorescence. Alternatively, a Siva protein can be detected in vivo in a subject by introducing into the subject a labeled anti-Siva antibody. For example, the antibody can be labeled with a radioactive marker whose presence and location in a subject can be detected by standard imaging techniques.

The invention also encompasses kits for detecting the presence of Siva in a biological sample. For example, the kit can comprise a labeled or labelable compound or agent capable of detecting Siva polypeptide or mRNA in a biological sample; means for determining the amount of Siva in the sample; and means for comparing the amount of Siva in the sample with a standard. The compound or agent can be packaged in a suitable container. The kit can further comprise instructions for using the kit to detect Siva mRNA or protein.

The methods of the invention can also be used to detect genetic lesions in a Siva gene, thereby determining if a subject with the lesioned gene is at risk for a disorder characterized by aberrant or abnormal Siva nucleic acid expression or Siva protein activity as defined herein. In preferred embodiments, the methods include detecting, in a sample of cells from the subject, the presence or absence of a genetic lesion characterized by at least one of an alteration affecting the integrity of a gene encoding a Siva protein, or the misexpression of the Siva gene. For example, such genetic lesions can be detected by ascertaining the existence of at least one of 1) a deletion of one or more nucleotides from a Siva gene; 2) an addition of one or more nucleotides to a Siva gene; 3) a substitution of one or more nucleotides of a Siva gene, 4) a chromosomal rearrangement of a Siva gene; 5) an alteration in the level of a messenger RNA transcript of a Siva gene, 6) aberrant modification of a Siva gene, such as of the methylation pattern of the genomic DNA, 7) the presence of a non-wild type splicing pattern of a messenger RNA transcript of a Siva gene, 8) a non-wild type level of a Siva-protein, 9) allelic loss of a Siva gene, and 10) inappropriate post-translational modification of a Siva-protein. As described herein, there are a large number of assay techniques known in the art which can be used for detecting lesions in a Siva gene.

In certain embodiments, detection of the lesion involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the Siva-gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a Siva gene under conditions such that hybridization and amplification of the Siva-gene (if present) occurs, and detecting the presence or absence of an amplification product, or detecting the size of the amplification product and comparing the length to a control sample.

In an alternative embodiment, mutations in a Siva gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the Siva gene and detect mutations by comparing the sequence of the sample Siva with the corresponding wild-type (control) sequence. Examples of sequencing reactions include those based on techniques developed by Maxim and Gilbert ((1977) *PNAS* 74:560) or Sanger ((1977) *PNAS* 74:5463). A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the Siva gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286–295), electrophoretic mobility of mutant and wild type nucleic acid is compared (Orita et al. (1989) *PNAS* 86:2766; Cotton (1993) *Mutat Res* 285:125–144; and Hayashi (1992) *Genet Anal Tech Appl* 9:73–79), and movement of mutant or wild-type fragments in polyacrylamide gels containing a gradient of denaturant is assayed using denaturing gradient gel electrophoresis (Myers et al (1985) *Nature* 313:495). Examples of other techniques for detecting point mutations include, selective oligonucleotide hybridization, selective amplification, and selective primer extension.

c. Methods of Treatment

Another aspect of the invention pertains to methods for treating a subject, e.g., a human, having a disease or disorder characterized by (or associated with) aberrant or abnormal Siva nucleic acid expression and/or Siva polypeptide activity. These methods include the step of administering a Siva modulator to the subject such that treatment occurs. The language "aberrant or abnormal Siva expression" refers to expression of a non-wild-type Siva polypeptide or a non-wild-type level of expression of a Siva polypeptide. Aberrant or abnormal Siva activity refers to a non-wild-type Siva activity or a non-wild-type level of Siva activity. As the Siva polypeptide is involved in an apoptotic pathway, aberrant or abnormal Siva activity or expression interferes with the normal apoptotic functions, e.g., apoptotic function in immune cells. Non-limiting examples of disorders or diseases characterized by or associated with abnormal or aberrant Siva activity or expression in immune cells include proliferative disorders such as malignant lymphomas, e.g., Non-Hodgkin's lymphomas, Hodgkin's disease, leukemias such as acute and chronic leukemias and other immune cells disorders described in Robbins, S. L. et al. Pathologic Basis of Disease, 3rd ed. (W.B. Saunders Company, Philadelphia, 1984) pp. 653–704. Other non-limiting examples of disorders or diseases characterized by or associated with abnormal or aberrant Siva activity or expression in immune cells include autoimmune diseases such as diabetes mellitus, arthritis (including rheumatoid arthritis, juvenile rheumatoid arthritis, osteoarthritis, psoriatic arthritis), multiple sclerosis, myasthenia gravis, systemic lupus crythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia arcata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic enccphalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary binary cirrhosis, uveitis posterior, and interstitial lung fibrosis). The terms "treating" or "treatment", as used herein, refer to reduction or alleviation of at least one adverse effect or symptom of a disorder or disease, e.g., a disorder or disease characterized by or associated with abnormal or aberrant Siva polypeptide activity and/or Siva nucleic acid expression.

As used herein, a Siva modulator is a molecule which can modulate Siva nucleic acid expression and/or Siva protein activity. For example, a Siva modulator can modulate, e.g., upregulate (activate) or downregulate (suppress), Siva nucleic acid expression. In another example, an Siva modulator can modulate (e.g., stimulate or inhibit) Siva protein activity. If it is desirable to treat a disorder or disease characterized by (or associated with) aberrant or abnormal (non-wild-type) Siva nucleic acid expression and/or Siva protein activity by inhibiting Siva nucleic acid expression, a Siva modulator can be an antisense molecule, e.g., a ribozyme, as described herein. Examples of antisense molecules which can be used to inhibit Siva nucleic acid expression include antisense molecules which are complementary to a portion of the 5' untranslated region of SEQ ID NO:1 or SEQ ID NO:3 which also includes the start codon and antisense molecules which are complementary to a portion of the 3' untranslated region of SEQ ID NO:1 or SEQ ID NO:3. A Siva modulator which inhibits Siva nucleic acid expression can also be a small molecule or other drug, e.g., a small molecule or drug identified using the screening assays described herein, which inhibits Siva nucleic acid expression. Siva modulators which inhibit Siva nucleic acid expression can be used to treat disorders for which it is desirable to increase immune cell survival. Examples of such disorders include immunodeficiency diseases, such as primary immunodeficiencies (including, severe combined immunodeficiency, adenosine deaminase deficiency, purine nucleoside phosphorylase deficiency, MHC class II deficiency, reticular dysgenesis, X-linked agammaglobulinemia, X-linked hypogammaglobulinemia, Ig deficiency with increased IgM, Ig heavy chain-gene deletions, k-chain deficiency IgA deficiency, selective deficiency of IgG subclass, common variable immunodeficiency, transient hypogammaglobulinemia of infancy, Wiskott-Aldrich syndrome, ataxia telangiectasia, DiGeorge syndrome, Bloom syndrome, Fanconi anemia, and Down syndrome-related immunodeficiency, as well as other syndromes associated with immunodeficiency) and immunodeficiencies resulting from other causes, such as HIV disease/AIDS. In addition, Siva modulators which inhibit Siva nucleic acid expression can also be used to increase immune cell survival to thereby promote cellular responses to tumors, or pathogens, such as viruses, bacteria, fungi, and parasites.

If it is desirable to treat a disease or disorder characterized by (or associated with) aberrant or abnormal (non-wild-type) Siva nucleic acid expression and/or Siva protein activity by stimulating Siva nucleic acid expression, a Siva modulator can be, for example, a nucleic acid molecule encoding Siva (e.g., a nucleic acid molecule comprising a nucleotide sequence homologous to the nucleotide sequence of SEQ ID NO:1 or SEQ ID NO:3) or a small molecule or other drug, e.g., a small molecule (peptide) or drug identified using the screening assays described herein, which stimulates Siva nucleic acid expression. Siva modulators which promote Siva nucleic acid expression can be used to treat disorders for which it is desirable to decrease immune cell survival. Examples of such disorders include proliferative disorders as described herein, graft-versus-host disease, and allergy.

Alternatively, if it is desirable to treat a disease or disorder characterized by (or associated with) aberrant or abnormal (non-wild-type) Siva nucleic acid expression and/or Siva polypeptide activity by inhibiting Siva protein activity, a Siva modulator can be an anti-Siva antibody or a small molecule or other drug, e.g., a small molecule or drug identified using the screening assays described herein, which inhibits Siva protein activity. Siva modulators which inhibit Siva protein activity can be used to treat disorders for which it is desirable to increase immune cell survival. Examples of such disorders are described herein.

If it is desirable to treat a disease or disorder characterized by (or associated with) aberrant or abnormal (non-wild-type) Siva nucleic acid expression and/or Siva protein activity by stimulating Siva protein activity, a Siva modulator can be an active Siva protein or portion thereof (e.g., a Siva protein or portion thereof having an amino acid sequence which is homologous to the amino acid sequence of SEQ ID NO:2 or SEQ ID NO:4 or a portion thereof) or a small molecule or other drug, e.g., a small molecule or drug identified using the screening assays described herein, which stimulates Siva protein activity. Siva modulators which promote Siva protein activity can be used to treat disorders for which it is desirable to decrease immune cell survival. Examples of such disorders are described herein.

In addition, a subject having a proliferative disorder, e.g., a proliferative disorder of an immune cell can be treated according to the present invention by administering to the subject a Siva protein or portion thereof or a nucleic acid encoding a Siva protein or portion thereof such that treatment occurs. In addition, the Siva modulators of the invention can be used to inhibit metastasis of tumor cells to thereby further treat proliferative disorders. Similarly, a subject having autoimmune disorder or disease can be treated according to the present invention by administering to the subject a Siva protein or portion thereof or a nucleic acid encoding a Siva protein or portion thereof such that treatment occurs.

Other aspects of the invention pertain to methods for modulating a cell associated activity. These methods include contacting the cell with an agent (or a composition which includes an effective amount of an agent) which modulates Siva protein activity or Siva nucleic acid expression such that a cell associated activity is altered relative to a cell associated activity of the cell in the absence of the agent. As used herein, "a cell associated activity" refers to a normal or abnormal activity or function of a cell. Examples of cell associated activities include proliferation, migration, differentiation, production or secretion of molecules, such as proteins, and cell survival. In a preferred embodiment, the cell is an immune cell. The term "altered" as used herein refers to a change, e.g., an increase or decrease, of a cell associated activity. In one embodiment, the agent stimulates Siva protein activity or Siva nucleic acid expression. Examples of such stimulatory agents include an active Siva protein, a nucleic acid molecule encoding Siva that has been introduced into the cell, and a modulatory agent which stimulates Siva protein activity or Siva nucleic acid expression and which is identified using the drug screening assays described herein. In another embodiment, the agent inhibits Siva protein activity or Siva nucleic acid expression. Examples of such inhibitory agents include an antisense Siva nucleic acid molecule, an anti-Siva antibody, and a modulatory agent which inhibits Siva protein activity or Siva nucleic acid expression and which is identified using the drug screening assays described herein. These modulatory methods can be performed in vitro (e.g., by culturing the cell with the agent) or, alternatively, in vivo (e.g., by administering the agent to a subject). In a preferred embodiment, the modulatory methods are performed in vivo, i.e., the cell is present within a subject, e.g., a mammal, e.g., a human, and the subject has a disorder or disease characterized by or associated with abnormal or aberrant Siva protein activity or Siva nucleic acid expression.

A nucleic acid molecule, a polypeptide, a Siva modulator, a compound etc. used in the methods of treatment can be incorporated into an appropriate pharmaceutical composition described herein and administered to the subject through a route which allows the molecule, polypeptide, modulator, or compound etc. to perform its intended function. Examples of routes of administration are also described herein under subsection IV.

The present invention is further illustrated by the following examples which should not be construed as limiting. The contents of all cited references (including literature references, issued patents, published patent applications, and co-pending patent applications) cited throughout this application are hereby expressly incorporated by reference.

EXAMPLES

The following materials and methods were used in the Examples:

Plasmids and Transfectants

The generation of mock, human CD27 and human CD70 transfectants in the murine pre-B 300-19 cell line has been described elsewhere (Kobata, T. et al. (1994) *J. Immunol.* 153:5422–5432; Kobata, T. et al. (1995) *PNAS* 92:11249–11253). CD27 cytoplasmic tail (residues 192–240) was subcloned in frame at the 3' end of the Gal4 DNA binding domain of the yeast shuttle vector pAS2 at the Nde1 and BamH1 sites. CD27WT (full length) was subcloned into the RcCMV vector at the Hind3 and Xba1 sites. Siva-1 sequence (nucleotides 1–567) was fused in frame to the C-terminus of GFP using the EcoR1 site in the pEGFPC1 plasmid (Clontech, Palo Alto, Calif.). Since PCR was used to generate specific restriction sites, all the fusions constructed were confirmed by sequencing the coding frame.

Yeast two Hybrid Screening

The procedures followed were essentially according to the manufacture's instructions (Clontech manual, Palo Alto, Calif.). The yeast strain HF7C was transfected with pAS2CD27CT and pGADGH2 containing the HeLa cDNA library. Potential CD27CT interacting clones were selected based on their ability to grow in the absence of Leu, Tyr and His and for their capacity to turn blue in the presence of X-gal. Positive colonies were picked and the library derived plasmids were recovered by transforming HB101 bacteria grown on minimal plates in the presence of ampicillin and absence of Leu. The interacting clones were confirmed by re-transfecting HF7C along with the pAS2CD27CT. A GenBank search with the DNA and protein sequence of H2 confirmed that it was novel. The H2 insert was then used to screen a HeLa cDNA ($\lambda$ zap1) and a 5' stretch human thymus cDNA ($\lambda$gt11) library to obtain the full length Siva-1 cDNA. All the vectors and libraries were purchased from Clontech, Palo Alto, Calif.

Northern Blot Analysis and Transient Transfections

Pre-made Northern blots (2 $\mu$g of poly(A)+RNA/lane) representing various human tissues and cell lines (Clontech, Palo Alto, Calif.) were probed with the H2 insert labeled with $^{32}$P-ATP using the Quick Prime kit (Pharmacia, Piscataway, N.J.). Both pre-hybridization and hybridization were carried out at 42° C. in the presence of formamide. Suspension cells were transfected using the lipofectamine reagent (Life Technologies, Gaithersburg, Md.). Adherent cells were transfected using the calcium phosphate procedure. Transfection efficiencies with both procedures ranged from 15–20%.

DNA Fragmentation Assay

Cells were lysed (0.4% Triton X-100, 4 mM EDTA in 25 mM Tris pH 7.5). Supernatant was treated with phenol:chloroform and the DNA precipitated. Prior to separation of DNA on agarose, it was treated with RNAse.

Immunoprecipitations and Western blotting 293 cells (transformed, human embryonal kidney cells) were detached using PBS containing 2 mM EDTA, collected and lysed (1% NP40 and 150 mM NaCl in 20 mM Tris pH 7.5) in the presence of protease inhibitors. Supernatant was precleared with anti-mouse Ig coupled to sepharose beads and immunoprecipitation was carried out using anti-CD27 monoclonal antibody (IA4, 3 $\mu$g/ml) and anti-mouse IgG beads. Whole cell lysates were prepared using RIPA buffer (1% NP40, 1% DOC and 0.1% SDS). Proteins were separated on 12% SDS-PAGE, transferred to a nitrocellulose membrane, blocked with 3% BSA and immunoblotted with anti-GFP rabbit antiserum (1:1000) and developed using the ECL reagent.

Example I

CD27 Effects Cellular Apoptosis

Although several of the TNFR family members are known to induce apoptosis (Smith, C. A. et al. (1994) *Cell* 76:959–962), there has been no report to date as to whether CD27 is capable of effecting this cell function. In order to test this, Ramos, a B cell line which expresses high levels of surface CD27 was cultured at relatively low cell density for 2 days with varying concentrations of live CD70 or mock transfectants. Apoptosis was only observed after culture in the presence of CD70 transfectants, as assessed by DNA fragmentation. Under similar conditions, no fragmented DNA was observed when Ramos, mock and CD70 transfectant cells were cultured alone.

In order to be certain that CD27-bearing cells and not the transfectant cells were undergoing apoptosis, the experiment was repeated using the same transfectants fixed with formaldehyde. Once again, pre-fixed CD70 transfectants but not the mock transfectants were capable of inducing apoptosis in Ramos, Raji, another B cell line, although this effect was less pronounced using the CD27 transfectant. Pre-fixing the transfectants and/or culturing the cells alone did not result in DNA fragmentation.

Since ligation of surface IgM in activated B cells is also known to cause cell death (Tsubata, T. et al. (1993) *Nature* 364:645–648; Valentine, M. A. and Licciardi, K. A. (1992) *Eur. J. Immunol.* 22:3141–3148), experiments were performed to determine whether co-ligation of CD27 would enhance this effect. It was found that co-culture with CD70 transfectants and ligation of surface Ig receptors resulted in marked enhancement in cell death in Ramos and CD27 transfectant but was not apparent in Raji cells. Ligation of CD27 induces apoptosis in normal human peripheral blood lymphocytes (PBLs) pre-activated with PHA and IL2.

The B cell lines Ramos and Raji express on their surface relatively high levels of both CD27 and CD70 but do not undergo apoptosis under normal cell culture conditions. This could be due to the relatively low cell density used for routine cell culture, which may not permit the interaction between CD27 and CD70 to reach the requisite threshold. In the experimental conditions described herein, the amount of available CD70 to Ramos cell cultures is increased by several orders of magnitude, thus overcoming the threshold barrier and resulting in apoptosis of CD27-bearing cells. This is supported by the observation that Ramos or Raji cells grown to relatively high cell density ($>1.0 \times 10^6$ cells/ml), results in increased background apoptosis even in the presence of optimum amounts of nutrients.

B-cell cancers such as Non-Hodgkin's lymphoma and B-CLL do not undergo apoptosis, despite the high expression of both CD27 and CD70. This could be due to the fact that these cells release soluble CD27 (sCD27) (Ranheim, E. A. et al. (1995) *Blood* 85:3556–356; Van Oers, M. H. et al. (1993) *Blood* 82:3430–3436), which builds up in the body fluids, and possibly disrupts CD27-mediated apoptosis. Disruption of the binding between CD27 and CD70 by sCD27 is also likely to aid in metastasis, thus playing an accelerating role in the progress of these cancers.

Example II

Identification and Characterization of the Human Siva-1 Gene

The cytoplasmic tail of CD27 (CD27CT) is highly conserved between man and mouse (Camerini, D. et al. (1991) *J. Immunol.* 147:3165–3169; Gravestein, L. A. et al. (1993) *Eur. J. Immunol.* 23:943–950) suggesting its importance for the receptor function. In this example, the CD27CT was used as the bait for screening a HeLa cell cDNA library using the yeast two hybrid system. The Epstein-Barr virus transforming protein, LMP1 and its binding protein, Lap1 (TRAF3/CRAF) coding plasmids were used as the positive control in the yeast system (Valentine, M. A. and Licciardi, K. A. (1992) *Eur. J Immunol.* 22:3141–3148). Transfection of the yeast strain HF7C with pAS2LMP1 and pGADLap1 plasmids gave several robust colonies when selected on plates lacking Leu, Tyr and His and all of them turned blue in the presence of x-gal. One clone, H2, co-transfected with the CD27CT plasmid gave several slow growing slightly smaller size colonies that turned blue in the presence of x-gal, but not when transfected together with the LMP1 plasmid, clearly suggesting the preferential interaction between the CD27CT and H2 (Table 1).

TABLE 1

GROWTH AND INDUCTION OF β-GALACTOSIDASE IN THE YEAST STRAIN HF7C IN THE ABSENCE OF LEU, TYR, AND HIS

|  | pAS2LMP1 | | pAS2CD27CT | |
| --- | --- | --- | --- | --- |
|  | Colonies | Blue Color | Colonies | Blue Color |
| pGADLAP1 | ++++ | ++++ | None | — |
| pGADH2* | None | — | ++ | +++ |

*H2 related clones H1 and H7 also gave similar results. pAS2CD27CT and pGADH2 transfectants grown in the absence of Tyr and Leu respectively, did not turn blue in the presence of x-Gal.

Of the several positive clones, a GenBank search identified the clone H2 as novel. Full length cDNA sequence was obtained by further screening HeLa cell and human thymocyte cDNA libraries using the H2 insert from the pGADH2 plasmid. Translation of the open reading frame revealed the primary sequence to be 189 amino acids long (FIG. 1; SEQ ID NO:2). The initiation codon is defined by the upstream in-frame stop codon (starting at nucleotide-42 in FIG. 1 (nucleotide 42 in SEQ ID NO:1)). The coding region is followed by a stop codon (starting at nucleotide 568 in FIG. 1 (nucleotide 700 in SEQ ID NO:1)), a poly-adenylation signal (nucleotides 709 to 714 in FIG. 1 (nucleotides 841 to 846 of SEQ ID NO:1)). The protein having this amino acid sequence was designated "Siva" (after the Hindu god of destruction). As a putative splice variant of this protein was also identified, this Siva protein was designated "Siva-1". The nucleotide sequence encoding this protein is also referred to herein as "Siva-1" nucleic acid (FIG. 1; SEQ ID NO:1) and has been deposited with GenBank under Accession Number U2938.

Analysis of the Siva-1 primary amino acid sequence revealed an amino terminal region that has homology to the death domains of FADD and RIP. The alignment and homology calculations were determined using the program Clustal, where the amino acid size is also taken into consideration. The Siva-1 protein also shares homology with the death domain of TRADD (Hsu, H. et al. (1995) *Cell* 81:495–504).

The carboxy terminal region of Siva-1 is rich in cysteines and forms a B-Box like ring finger (amino acid residues 128–159 of SEQ ID NO:2 also shown as a separate sequence identification number SEQ ID NO:9) (Freemont, P. S. (1993) *Ann. N.Y. Acad. Sci.* 684:174–192). The B-Box region of Siva-1, however, lacks histidine. The amino terminal ring finger and the carboxy terminal coiled-coil domain structures, which are characteristic of other B-Box-containing proteins (Freemont, P. S. (1993) *Ann. N.Y Acad. Sci.* 684:174–192), are absent in Siva-1. Instead, Siva-1 is flanked by additional cysteine residues in the carboxy terminus that can form a zinc finger (amino acid residues 164–184 of SEQ ID NO:2 also shown as a separate sequence identification number SEQ ID NO:8), which also lacks histidine. Alternately, the cysteine rich region of Siva-1 can represent a novel metal binding motif involved in either protein-protein or protein-DNA interactions. The architecture of Siva-1 is unlike any of the molecules so far known to bind to the cytoplasmic tails of other TNFR family members.

Example III

Tissue Expression of the Human Siva-1 Gene

Multiple human tissue northern blot analysis revealed the presence of varying amounts of 0.8 kb Siva-1 mRNA in all the represented tissues including spleen, thymus, prostate, testis, ovary, small intestine, colon, and peripheral blood lymphocytes as well as several cell lines including HeLa cells (ATCC Accession No. CCL 2: human cervical carcinoma cell line), Raji cells (ATCC Accession No. CCL 86: human Burkitt lymphoma cell line), HL60 cells (ATCC Accession No. CCL 240: human promyelocyte cell line), K562 cells (ATCC Accession No. CCL 243: human erythroleukemia cell line), MOTL-4 cells (ATCC Accession No. CRL 1582: human acute lymphoblastic leukemia cell line), SW480 cells (ATCC Accession No. CCL 228: human colorectal adenocarcinoma cell line), A549 cells (ATCC Accession No. CCL 185: human lung carcinoma cell line), and G-361 cells (ATCC Accession No. CRL 1424: human malignant melanoma cell line). Maximum mRNA expression was seen in thymus and the least in colon.

Example IV

Expression of Recombinant Human Siva-1 Protein in Human Cells

Although the results from the yeast two hybrid assay described above suggests a direct interaction between the CD27 cytoplasmic tail and Siva-1, the association between the two molecules was confirmed by transiently expressing (2 days) CD27WT (full length) DNA and Siva-1 fused to the bacterial green fluorescence protein (GFP-Siva-1) and GFP alone in 293 embryonal renal cells. Cell lysates were prepared using mild non-ionic detergent like NP-40 and the CD27 receptor complexes were immunoprecipitated using anti-CD27 monoclonal antibody (1A4). The expression of GFP-Siva and GFP were similar as determined from the anti-GFP immunoblot. CD27 was found to co-precipitate GFP-Siva-1 but not GFP.

Example V

Overexpression of Siva-1 Induces Apoptosis

Since CD27 induces cell death and since its binding protein, Siva-1, has a region with significant homology to the death domains, experiments were performed to determine ether overexpression of Siva-1 causes significant cellular apoptosis. GFP and GFP-Siva-1 were transiently expressed in Jurkat, Raji, SKW, Ramos and 293 cell lines for two days and the percentage of dead cells that were fluorescing green was measured. In general, most of the cells expressing GFP-Siva-1 looked unhealthy, very small, and with an irregular cell border when compared with cells expressing GFP. In every cell line tested, the percentage of GFP-Siva-1 transfected dead cells were 2–3 times higher on comparison with those transfected with GFP alone. In the case of the adherent cell line 293, the β-galactosidase gene was expressed along with GFP and GFP-Siva-1. β-galactosidase expression was visualized by x-gal and cell morphology was examined using the light microscope. Most of the cells expressing GFP-Siva-1 were much smaller and rounded (devoid of the cellular processes), clearly suggesting apoptosis. That this indeed is the case was confirmed by DNA fragmentation assay in 293 (adherent) and murine pre-B cell line (suspension). Electron microscopy performed on GFP and GFP-Siva-1 transfected 293 cells revealed the presence of cells with apoptotic bodies only in GFP-Siva-1 transfectants.

Thus, interaction between CD27 and CD70 is sufficient to elicit the apoptotic function of CD27. In the absence of crucial complementary signals, it is likely that engagement of CD27, especially in activated T and B cells that express CD27 and CD70, results in apoptosis. In situations of chronic activation, CD27-induced apoptosis likely plays an important role in maintaining self-tolerance and keeping in check activated T and B cells, which may contribute to some autoimmune diseases. In the case of multiple sclerosis, where elevated levels of soluble CD27 (sCD27) have been reported, it is possible that these elevations inhibit the regulatory or other effects of CD70 expressing T and B cells (Hinztmen, R. Q. et al. (1991) *J. Neuroimmunol.* 35:211–218).

Example VI

Identification of the Human Siva-2 Gene

While screening a human thymus cDNA library in an attempt to obtain a full length H2 clone, a second Siva gene, designated Siva-2, was identified. Upon comparing of their nucleotide sequences, the nucleotide sequence of Siva-2 was found to be the same as that of Siva-1 except for an in-frame deletion of nucleotides 157–351 spanning most of the death domain homology region. Thus, Siva-2 appears to be an alternate splice form of Siva-1.

To confirm that Siva-2 mRNA exists, RTPCR, using a 5' forward primer spanning the very beginning of Siva-1 and a 3' reverse primer matching the 3' end of Siva-1, was performed on RNA (treated extensively with DNAse) samples obtained from 293, Raji, HeLa, and thymus cells. The existence of two forms of Siva, an abundant form at about 600 bp (Siva-1) and a less abundant form at about 400 bp (Siva-2) was apparent in both thymus and Raji cells. The nucleotide sequence of Siva-2 is shown in SEQ ID NO:3 and the deduced amino acid sequence is shown in SEQ ID NO:4.

Thus far, two types of molecules that interact with various TNFR family members have surfaced. One group comprises the death domain containing proteins-TRADD, FADD and RIP which interact with Fas and TNFRI (Hsu, H. et al. (1995) *Cell* 81:505–512; Chinnaiyan, A. M. et al. (1995) *Cell* 81:505–512; Stanger, Z. B. et al. (1995) *Cell* 81:513–523; Hsu, H. et al. (1996) *Immunity* 4:387–396). TRAFs form the second group, characterized by the zinc finger domains and interact with TNFRII, CD40 and LMP1 (Mosialos, G. et al. (1995) *Cell* 80:389–399; Rothe, M. et al. (1995) *Science* 269:1424–1427; Hsu, H et al. (1994) *J. Biol. Chem.* 269:30069–30072; Cheng, G. et al. (1995) *Science* 267:1594–1498). In comparison, Siva does not appear to fall into either of these categories. Using the Clustal program that takes into consideration both the size and hydrophobicity of amino acids, a region in Siva homologous to the known death domains of FADD and RIP was identified. Although overall homology between the three is high, identical homology is low. Dendrogram analysis clearly places Siva outside all of the known DD containing proteins. The homologies reported here are comparable to those calculated for TRADD/FADD and TRADD/RIP and are higher than those for the DD of Reaper and other DD containing proteins (Cleveland, J. L. and Ihle, J. N. (1995) *Cell* 81:479–482). NMR structure of Fas DD revealed the presence of six antiparallel, amphipathic α helices, and a similar structure has been proposed for other DDs (Huang, B. et al. (1996) *Nature* 384:638–641). However, based on secondary structure predictions, the DDHR of Siva appears to lack at least 4 of these helices and thus could possibility be structurally different from that of the DD of Fas and its distant relative Reaper. An important consideration is that all DDs do not appear to be similar in terms of cellular function. For example, the DD of FADD is required for binding of FADD to FAS DD, but not for induction of apoptosis (Stanger, Z. B. et al. (1995) *Cell* 81:513–523; Grimm, S. et al. (1996) *PNAS* 93:10923–10927). TRADD DD however is required for eliciting both apoptosis and activation of the transcription factor NFkB (Chinnaiyan, A. M. et al. (1995) *Cell* 81:505–512; Park, A. and Baichwal, R. (1996) *J. Biol. Chem.* 271:9858–9862). In case of the Drosophila protein Reaper, mutations carried out in the DD region similar to that of Fas DD, does not abrogate the potent apoptotic activity of the protein (Chen, P. et al. (1996) *J. Biol Chem.* 271:25735–25737).

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. An isolated nucleic acid molecule comprising a nucleotide sequence encoding a protein that modulates apoptosis in a cell, wherein said nucleic acid molecule hybridizes to the nucleic acid molecule shown in SEQ ID. NO: 1 or SEQ ID NO:3 or a complement thereof under conditions of about 6× sodium chloride/sodium citrate (SSC) at a temperature of about 45° C. followed by one or more washes in 0.2×SSC, 0.1% SDS at a temperature of about 65° C.

2. The isolated nucleic acid molecule of claim 1, wherein the protein comprises an amino acid sequence shown in SEQ ID NO:2 or SEQ ID NO:4.

3. The isolated nucleic acid molecule of claim 1 the cell is a CD27-bearing cell.

4. The isolated nucleic acid molecule of claim 1 which consists of the nucleotide sequence shown in SEQ ID NO:1 or SEQ ID NO:3.

5. A vector comprising the nucleic acid molecule of claim 1.

6. A host cell containing the vector of claim 5.

7. A method for producing Siva protein comprising culturing the host cell of claim 6 in a suitable medium and isolating the protein product.

8. An isolated nucleic acid molecule comprising a nucleotide sequence encoding a protein that modulates apoptosis in a cell wherein the protein or portion thereof comprises an amino acid sequence shown in SEQ ID NO:2 or SEQ ID NO:4.

9. An isolated nucleic acid molecule encoding a protein comprising one or more of the following domains:
   a) a death domain homology region shown in the amino acid sequence of SEQ ID NO:7
   b) a zinc finger domain shown in the amino acid sequence of SEQ ID NO:8; and
   c) a B-Box like ring finger domain shown in the amino acid sequence of SEQ ID NO:9, wherein said protein modulates apoptosis.

10. The isolated nucleic acid molecule of claim 9, comprising the coding region shown in nucleotides 133–169 of the nucleotide sequence of SEQ ID NO:1.

11. The isolated nucleic acid molecule of claim 9, comprising the coding region shown in nucleotides 133–504 of the nucleotide sequence of SEQ ID NO:3.

12. The isolated nucleic acid molecule of claim 9 encoding a fusion protein.

13. An isolated nucleic acid molecule comprising at least 15 to about 75 contiguous nucleotides of the coding region of SEQ ID NO:1 shown in nucleotides 133–699 or the coding region of SEQ ID NO:3 shown in nucleotides 133–504 which hybridizes to at least a portion of a second nucleic acid molecule under conditions of about 6× sodium chloride/sodium citrate (SSC) at a temperature of about 45° C. followed by one or more washes in 0.2×SSC, 0.1% SDS at a temperature of about 50–65° C., wherein the second nucleic acid molecule encodes at least a portion of a Siva protein shown in SEQ ID NO:2 or SEQ ID NO:4, that modulate apoptosis in a cell.

14. An isolated nucleic acid molecule of claim 13, which is at least 75 nucleotides in length.

15. An isolated nucleic acid molecule comprising a nucleotide sequence at least 500 nucleotides in length, wherein said nucleic acid molecule hybridizes to the nucleic acid molecule shown in SEQ ID. NO: 1 or SEQ ID NO:3 or a complement thereof under conditions of about 6× sodium chloride/sodium citrate (SSC) at a temperature of about 45° C. followed by one or more washes in 0.2×SSC, 0.1% SDS at a temperature of about 65° C.

16. An isolated nucleic acid molecule comprising a nucleotide sequence at least 500 nucleotides in length and encoding a protein, wherein the protein comprises an amino acid sequence shown in SEQ ID NO:2 or SEQ ID NO:4 and modulates apoptosis in a cell.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 885 base pairs
        (B) TYPE: nucleic acid
        (C) STRANDEDNESS: single
        (D) TOPOLOGY: linear (ii) MOLECULE TYPE: cDNA (v) FRAGMENT TYPE: internal (ix) FEATURE:
        (A) NAME/KEY: CDS
        (B) LOCATION: 133..699

(xi) SEQUENCE DESCRIPTION: SEQ ID NO:1:

```
AGCCAAGCGT GGTGGCATGT GCCTGTAATC CCAGCTACTC AGGAGGCTGA GGCATGAGAA      60

TCTCTTGAAC CCCAGAGGTG TAGGTTGCAG TGAGCAGAGA TTGTGCCACT GCACTCCAGC     120

CTGGGCGACA GC ATG AGG CGG CCG GGG AGC TGC GTA GCT CCC GGC CCC         168
              Met Arg Arg Pro Gly Ser Cys Val Ala Pro Gly Pro
              1               5                  10

GCG GCC ATG CCC AAG CGG AGC TGC CCC TTC GCG GAC GTG GCC CCG CTA       216
Ala Ala Met Pro Lys Arg Ser Cys Pro Phe Ala Asp Val Ala Pro Leu
         15                  20                  25

CAG CTC AAG GTC CGC GTG AGC CAG AGG GAG TTG AGC CGC GGC GTG TGC       264
Gln Leu Lys Val Arg Val Ser Gln Arg Glu Leu Ser Arg Gly Val Cys
 30                  35                  40

GCC GAG CGC TAC TCG CAG GAG GTC TTC GAG AAG ACC AAG CGA CTC CTG       312
Ala Glu Arg Tyr Ser Gln Glu Val Phe Glu Lys Thr Lys Arg Leu Leu
 45                  50                  55                  60

TTC CTC GGG GCC CAG GCC TAC CTG GAC CAC GTG TGG GAT GAA GGC TGT       360
Phe Leu Gly Ala Gln Ala Tyr Leu Asp His Val Trp Asp Glu Gly Cys
                 65                  70                  75

GCC GTC GTT CAC CTG CCA GAG TCC CCA AAG CCT GGC CCT ACA GGG GCC       408
Ala Val Val His Leu Pro Glu Ser Pro Lys Pro Gly Pro Thr Gly Ala
             80                  85                  90

CCG AGG GCT GCA CGT GGG CAG ATG CTG ATT GGA CCA GAC GGC CGC CTG       456
Pro Arg Ala Ala Arg Gly Gln Met Leu Ile Gly Pro Asp Gly Arg Leu
         95                 100                 105

ATC AGG AGC CTT GGG CAG GCC TCC GAA GCT GAC CCA TCT GGG GTA GCG       504
Ile Arg Ser Leu Gly Gln Ala Ser Glu Ala Asp Pro Ser Gly Val Ala
     110                 115                 120

TCC ATT GCC TGT TCC TCA TGC GTG CGA GCC GTG GAT GGG AAG GCG GTC       552
Ser Ile Ala Cys Ser Ser Cys Val Arg Ala Val Asp Gly Lys Ala Val
125                 130                 135                 140

TGC GGT CAG TGT GAG CGA GCC CTG TGC GGG CAG TGT GTG CGC ACC TGC       600
Cys Gly Gln Cys Glu Arg Ala Leu Cys Gly Gln Cys Val Arg Thr Cys
                145                 150                 155

TGG GGC TGC GGC TCC GTG GCC TGT ACC CTG TGT GGC CTC GTG GAC TGC       648
Trp Gly Cys Gly Ser Val Ala Cys Thr Leu Cys Gly Leu Val Asp Cys
            160                 165                 170

AGT GAC ATG TAC GAG AAA GTG CTG TGC ACC AGC TGT GCC ATG TTC GAG       696
Ser Asp Met Tyr Glu Lys Val Leu Cys Thr Ser Cys Ala Met Phe Glu
            175                 180                 185

ACC TGAGGCTGGC TCAAGCCGGC TGCCTTCACC GGGAGCCACG CCGTGCATGG            749
Thr
```

```
CAGCCTTCCC TGGACGAGCG CTCGGTGTTC AGTGGGGTCG ACGGGAGGGG TGCCTTTTAC      809

ATGTTCTATT TTGTATCCTA ATGACAGAAT GAATAAACCT CTTTATATTT GCAAAAAAAA      869

AAAAAAAAAA CTCGAG                                                      885
```

(2) INFORMATION FOR SEQ ID NO:2:

(i) SEQUENCE CHARACTERISTICS:
        (A) LENGTH: 189 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Arg Pro Gly Ser Cys Val Ala Pro Gly Pro Ala Ala Met Pro
 1               5                  10                  15

Lys Arg Ser Cys Pro Phe Ala Asp Val Ala Pro Leu Gln Leu Lys Val
         20                  25                  30

Arg Val Ser Gln Arg Glu Leu Ser Arg Gly Val Cys Ala Glu Arg Tyr
     35                  40                  45

Ser Gln Glu Val Phe Glu Lys Thr Lys Arg Leu Leu Phe Leu Gly Ala
 50                  55                  60

Gln Ala Tyr Leu Asp His Val Trp Asp Glu Gly Cys Ala Val Val His
 65                  70                  75                  80

Leu Pro Glu Ser Pro Lys Pro Gly Pro Thr Gly Ala Pro Arg Ala Ala
         85                  90                  95

Arg Gly Gln Met Leu Ile Gly Pro Asp Gly Arg Leu Ile Arg Ser Leu
     100                 105                 110

Gly Gln Ala Ser Glu Ala Asp Pro Ser Gly Val Ala Ser Ile Ala Cys
 115                 120                 125

Ser Ser Cys Val Arg Ala Val Asp Gly Lys Ala Val Cys Gly Gln Cys
 130                 135                 140

Glu Arg Ala Leu Cys Gly Gln Cys Val Arg Thr Cys Trp Gly Cys Gly
 145                 150                 155                 160

Ser Val Ala Cys Thr Leu Cys Gly Leu Val Asp Cys Ser Asp Met Tyr
 165                 170                 175

Glu Lys Val Leu Cys Thr Ser Cys Ala Met Phe Glu Thr
         180                 185
```

(2) INFORMATION FOR SEQ ID NO:3:

(i) SEQUENCE CHARACTERISTICS:
        (A) LENGTH: 690 base pairs
        (B) TYPE: nucleic acid
        (C) STRANDEDNESS: single
        (D) TOPOLOGY: linear (ii) MOLECULE TYPE: cDNA (v) FRAGMENT TYPE: internal (ix) FEATURE:
        (A) NAME/KEY: CDS
        (B) LOCATION: 133..504

(xi) SEQUENCE DESCRIPTION: SEQ ID NO:3:

```
AGCCAAGCGT GGTGGCATGT GCCTGTAATC CCAGCTACTC AGGAGGCTGA GGCATGAGAA       60

TCTCTTGAAC CCCAGAGGTG TAGGTTGCAG TGAGCAGAGA TTGTGCCACT GCACTCCAGC      120

CTGGGCGACA GC ATG AGG CGG CCG GGG AGC TGC GTA GCT CCC GGC CCC          168
              Met Arg Arg Pro Gly Ser Cys Val Ala Pro Gly Pro
```

```
              1               5                 10
GCG GCC ATG CCC AAG CGG AGC TGC CCC TTC GCG GAC GTG GCC CCG CTA    216
Ala Ala Met Pro Lys Arg Ser Cys Pro Phe Ala Asp Val Ala Pro Leu
 15               20                  25

CAG CTC AAG GTC CGC GTG AGC CAG AGG GAG TTG AGC CGC GGC GTG TGC    264
Gln Leu Lys Val Arg Val Ser Gln Arg Glu Leu Ser Arg Gly Val Cys
         30                  35                  40

GCC GAG CGC TAC TCG CAG GAG GTC TTC GAC CCA TCT GGG GTA GCG TCC    312
Ala Glu Arg Tyr Ser Gln Glu Val Phe Asp Pro Ser Gly Val Ala Ser
 45                  50                  55                  60

ATT GCC TGT TCC TCA TGC GTG CGA GCC GTG GAT GGG AAG GCG GTC TGC    360
Ile Ala Cys Ser Ser Cys Val Arg Ala Val Asp Gly Lys Ala Val Cys
 65                  70                  75

GGT CAG TGT GAG CGA GCC CTG TGC GGG CAG TGT GTG CGC ACC TGC TGG    408
Gly Gln Cys Glu Arg Ala Leu Cys Gly Gln Cys Val Arg Thr Cys Trp
         80                  85                  90

GGC TGC GGC TCC GTG GCC TGT ACC CTG TGT GGC CTC GTG GAC TGC AGT    456
Gly Cys Gly Ser Val Ala Cys Thr Leu Cys Gly Leu Val Asp Cys Ser
 95                 100                 105

GAC ATG TAC GAG AAA GTG CTG TGC ACC AGC TGT GCC ATG TTC GAG ACC    504
Asp Met Tyr Glu Lys Val Leu Cys Thr Ser Cys Ala Met Phe Glu Thr
        110                 115                 120

TGAGGCTGGC TCAAGCCGGC TGCCTTCACC GGGAGCCACG CCGTGCATGG CAGCCTTCCC    564

TGGACGAGCG CTCGGTGTTC AGTGGGGTCG ACGGGAGGGG TGCCTTTTAC ATGTTCTATT    624

TTGTATCCTA ATGACAGAAT GAATAAACCT CTTTATATTT GCAAAAAAAA AAAAAAAAAA    684

CTCGAG                                                               690

(2) INFORMATION FOR SEQ ID NO:4:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO:4:

Met Arg Arg Pro Gly Ser Cys Val Ala Pro Gly Pro Ala Ala Met Pro
 1               5                  10                  15

Lys Arg Ser Cys Pro Phe Ala Asp Val Ala Pro Leu Gln Leu Lys Val
         20                  25                  30

Arg Val Ser Gln Arg Glu Leu Ser Arg Gly Val Cys Ala Glu Arg Tyr
 35                  40                  45

Ser Gln Glu Val Phe Asp Pro Ser Gly Val Ala Ser Ile Ala Cys Ser
         50                  55                  60

Ser Cys Val Arg Ala Val Asp Gly Lys Ala Val Cys Gly Gln Cys Glu
 65                  70                  75                  80

Arg Ala Leu Cys Gly Gln Cys Val Arg Thr Cys Trp Gly Cys Gly Ser
         85                  90                  95

Val Ala Cys Thr Leu Cys Gly Leu Val Asp Cys Ser Asp Met Tyr Glu
            100                 105                 110

Lys Val Leu Cys Thr Ser Cys Ala Met Phe Glu Thr
115                 120

(2) INFORMATION FOR SEQ ID NO:5:

(i) SEQUENCE CHARACTERISTICS:
        (A) LENGTH: 770 base pairs
        (B) TYPE: nucleic acid
```

(C) STRANDEDNESS: single
            (D) TOPOLOGY: linear (ii) MOLECULE TYPE: cDNA (ix) FEATURE:
            (A) NAME/KEY: CDS
            (B) LOCATION: 88..612

(xi) SEQUENCE DESCRIPTION: SEQ ID NO:5:

```
TTTGGCTCCG AGGCCAAGAA TTCGGCACGA GGGCTCGGCG CGCGGCGCGC TGCGCGCTGC      60

TGAAGGCTGT GTCTGGTACC CGCTACC ATG CCC AAG CGG AGC TGC CCG TTC         111
                              Met Pro Lys Arg Ser Cys Pro Phe
                               1               5

GCA GAC GCA GCC CCG CTC CAA CTC AAA GTC CAC GTG GGC CTG AAA GAG      159
Ala Asp Ala Ala Pro Leu Gln Leu Lys Val His Val Gly Leu Lys Glu
         10                  15                  20

CTG AGC CAC GGT GTG TTC GCC GAG CGC TAC TCA CGC GAG GTC TTC GAA      207
Leu Ser His Gly Val Phe Ala Glu Arg Tyr Ser Arg Glu Val Phe Glu
 25                  30                  35                  40

AGA ACC AAG CAG CTC CTT TTC CAA GGG GCT CGG GCC TAT AGA GAT CAC      255
Arg Thr Lys Gln Leu Leu Phe Gln Gly Ala Arg Ala Tyr Arg Asp His
                 45                  50                  55

ATA TCG AGC GAA GAT TGT TCC GTG AAC CAC CTG CAG GAG TCA CTG AAG      303
Ile Ser Ser Glu Asp Cys Ser Val Asn His Leu Gln Glu Ser Leu Lys
             60                  65                  70

TCT GGT GTG GTA GGA GCC CCT CAA CCT GCG AGG GGA CAG ATG TTG ATT      351
Ser Gly Val Val Gly Ala Pro Gln Pro Ala Arg Gly Gln Met Leu Ile
 75                  80                  85

GGA CCT GAT GGC CGA CTG ACA CGG TGC CAA GCT CAG GCC TCA GAA GGT      399
Gly Pro Asp Gly Arg Leu Thr Arg Cys Gln Ala Gln Ala Ser Glu Gly
             90                  95                 100

GGC CTT CCC AGG ACA GCG CCC ATC GCT TGT TCA TCG TGC ATG AGA TCT      447
Gly Leu Pro Arg Thr Ala Pro Ile Ala Cys Ser Ser Cys Met Arg Ser
105                 110                 115                 120

GTG GAT GGG AAG GCG GTC TGC AGC CAG TGC GAG CGG GCC CTG TGT GGG      495
Val Asp Gly Lys Ala Val Cys Ser Gln Cys Glu Arg Ala Leu Cys Gly
                125                 130                 135

CAG TGT GTA TAC ACC AGC TGG GGC TGC GGT GCT TTG GCC TGT GTG CTG      543
Gln Cys Val Tyr Thr Ser Trp Gly Cys Gly Ala Leu Ala Cys Val Leu
            140                 145                 150

TGT GGC CTT GCA GAC TAT GCC GAC GAT GGT GAG AAG ACA CTG TGC ACC      591
Cys Gly Leu Ala Asp Tyr Ala Asp Asp Gly Glu Lys Thr Leu Cys Thr
155                 160                 165

AGC TGT GCT ATG TTT GAA GCC TGAGGTGGCC ACAGACAGCA CAAGATGTTC         642
Ser Cys Ala Met Phe Glu Ala
170                 175

ACACTAAAGA GAGAGAAGGT GGCTTTTTAT ATGTTATGTT TTATACCCAG TAACAAGTGA    702

ATAAACCTCT TTATATTTGC AAAAAAAAAA AAAAAAAAA AAAAAAATTT CCGCGGCCGC     762

AAGCTTAT                                                             770
```

(2) INFORMATION FOR SEQ ID NO:6:

(i) SEQUENCE CHARACTERISTICS:
            (A) LENGTH: 175 amino acids
            (B) TYPE: amino acid
            (D) TOPOLOGY: linear (ii) MOLECULE TYPE: protein (xi) SEQUENCE DESCRIPTION: SEQ ID NO:6:

Met Pro Lys Arg Ser Cys Pro Phe Ala Asp Ala Ala Pro Leu Gln Leu

```
                  1               5              10              15
            Lys Val His Val Gly Leu Lys Glu Leu Ser His Gly Val Phe Ala Glu
                            20              25              30

Arg Tyr Ser Arg Glu Val Phe Glu Arg Thr Lys Gln Leu Leu Phe Gln
                 35              40              45

Gly Ala Arg Ala Tyr Arg Asp His Ile Ser Ser Glu Asp Cys Ser Val
                     50              55              60

Asn His Leu Gln Glu Ser Leu Lys Ser Gly Val Val Gly Ala Pro Gln
             65              70              75                           80

Pro Ala Arg Gly Gln Met Leu Ile Gly Pro Asp Gly Arg Leu Thr Arg
                 85              90              95

Cys Gln Ala Gln Ala Ser Glu Gly Gly Leu Pro Arg Thr Ala Pro Ile
                     100             105             110

Ala Cys Ser Ser Cys Met Arg Ser Val Asp Gly Lys Ala Val Cys Ser
             115             120             125

Gln Cys Glu Arg Ala Leu Cys Gly Gln Cys Val Tyr Thr Ser Trp Gly
                 130             135             140

Cys Gly Ala Leu Ala Cys Val Leu Cys Gly Leu Ala Asp Tyr Ala Asp
             145             150             155             160

Asp Gly Glu Lys Thr Leu Cys Thr Ser Cys Ala Met Phe Glu Ala
                 165             170             175
```

(2) INFORMATION FOR SEQ ID NO:7:

(i) SEQUENCE CHARACTERISTICS:
        (A) LENGTH: 75 amino acids
        (B) TYPE: amino acid
        (D) TOPOLOGY: linear (ii) MOLECULE TYPE: protein (xi) SEQUENCE DESCRIPTION: SEQ ID NO:7:

```
Leu Gly Ala Gln Ala Tyr Leu Asp His Val Trp Asp Glu Gly Cys Ala
 1               5              10              15

Val Val His Leu Pro Glu Ser Pro Lys Pro Gly Pro Thr Gly Ala Pro
     20              25              30

Arg Ala Ala Arg Gly Gln Met Leu Ile Gly Pro Asp Gly Arg Leu Ile
 35              40              45

Arg Ser Leu Gly Gln Ala Ser Glu Ala Asp Pro Ser Gly Val Ala Ser
     50              55              60

Ile Ala Cys Ser Ser Cys Val Arg Ala Val Asp
 65              70              75
```

(2) INFORMATION FOR SEQ ID NO:8:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:8:

```
Cys Thr Leu Cys Gly Leu Val Asp Cys Ser Asp Met Tyr Glu Lys Val
 1               5              10              15

Leu Cys Thr Ser Cys
     20
```

(2) INFORMATION FOR SEQ ID NO:9:

```
    (i) SEQUENCE CHARACTERISTICS:
        (A) LENGTH: 32 amino acids
        (B) TYPE: amino acid
        (D) TOPOLOGY: linear (ii) MOLECULE TYPE: protein (xi) SEQUENCE DESCRIPTION: SEQ ID NO:9:

Cys Ser Ser Cys Val Arg Ala Val Asp Gly Lys Ala Val Cys Gly Gln
 1               5                  10                  15

Cys Glu Arg Ala Leu Cys Gly Gln Cys Val Arg Thr Cys Trp Gly Cys
        20                  25                  30

(2) INFORMATION FOR SEQ ID NO:10:

(i) SEQUENCE CHARACTERISTICS:
        (A) LENGTH: 65 amino acids
        (B) TYPE: amino acid
        (D) TOPOLOGY: linear (ii) MOLECULE TYPE: protein (xi) SEQUENCE DESCRIPTION: SEQ ID NO:10:

Asp Pro Ser Gly Val Ala Ser Ile Ala Cys Ser Cys Val Arg Ala
 1               5                  10                  15

Val Asp Gly Lys Ala Val Cys Gly Gln Cys Glu Arg Ala Leu Cys Gly
        20                  25                  30

Gln Cys Val Arg Thr Cys Trp Gly Cys Gly Ser Val Ala Cys Thr Leu
 35                  40                  45

Cys Gly Leu Val Asp Cys Ser Asp Met Tyr Glu Lys Val Leu Cys Thr
        50                  55                  60

Ser (2) INFORMATION FOR SEQ ID NO:11:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:11:

Cys Thr Leu Cys Gly Leu Val Asp Cys Ser Asp Met Tyr Glu Lys Val
 1               5                  10                  15

Leu Cys Thr Ser Cys
        20

(2) INFORMATION FOR SEQ ID NO:12:

(i) SEQUENCE CHARACTERISTICS:
        (A) LENGTH: 32 amino acids
        (B) TYPE: amino acid
        (D) TOPOLOGY: linear (ii) MOLECULE TYPE: protein (xi) SEQUENCE DESCRIPTION: SEQ ID NO:12:

Cys Ser Ser Cys Val Arg Ala Val Asp Gly Lys Ala Val Cys Gly Gln
 1               5                  10                  15

Cys Glu Arg Ala Leu Cys Gly Gln Cys Val Arg Thr Cys Trp Gly Cys
        20                  25                  30
```